(12) United States Patent
Chae et al.

(10) Patent No.: US 11,534,111 B2
(45) Date of Patent: Dec. 27, 2022

(54) SENSOR APPLICATOR ASSEMBLY FOR CONTINUOUS GLUCOSE MONITORING SYSTEM

(71) Applicant: I-SENS, INC., Seoul (KR)

(72) Inventors: Kyung Chul Chae, Gyeonggi-do (KR); Hyun Ho Choi, Seoul (KR); Goang Yel Ryu, Gyeonggi-do (KR); Ji Hoon Wang, Gyeonggi-do (KR); Young Jea Kang, Seoul (KR)

(73) Assignee: I-SENS, INC., Seoul (KR)

( * ) Notice: Subject to any disclaimer, the term of this patent is extended or adjusted under 35 U.S.C. 154(b) by 50 days.

(21) Appl. No.: 16/618,365

(22) PCT Filed: Jun. 1, 2018

(86) PCT No.: PCT/KR2018/006319
§ 371 (c)(1),
(2) Date: Dec. 1, 2019

(87) PCT Pub. No.: WO2018/222015
PCT Pub. Date: Dec. 6, 2018

(65) Prior Publication Data
US 2021/0137424 A1 May 13, 2021

(30) Foreign Application Priority Data
Jun. 2, 2017 (KR) .................. 10-2017-0068964
Jun. 1, 2018 (KR) .................. 10-2018-0063373

(51) Int. Cl.
*A61B 5/00* (2006.01)
*A61B 5/145* (2006.01)
(Continued)

(52) U.S. Cl.
CPC ........ *A61B 5/68335* (2017.08); *A61B 5/0002* (2013.01); *A61B 5/0004* (2013.01);
(Continued)

(58) Field of Classification Search
CPC . A61B 5/68335; A61B 5/0002; A61B 5/0004; A61B 5/14532; A61B 5/150244;
(Continued)

(56) References Cited

U.S. PATENT DOCUMENTS

| 2004/0133164 A1 | 7/2004 | Funderburk et al. |
| 2008/0114280 A1 | 5/2008 | Stafford |

(Continued)

FOREIGN PATENT DOCUMENTS

| EP | 1639942 | 3/2006 |
| EP | 2 327 984 | 6/2011 |

(Continued)

OTHER PUBLICATIONS

International Search Report for PCT/KR2018/006319 dated Sep. 7, 2018 and its English translation from WIPO (now published as WO2018/222015).

(Continued)

*Primary Examiner* — Daniel L Cerioni
*Assistant Examiner* — Deirdre M Willgohs
(74) *Attorney, Agent, or Firm* — Ladas & Parry, LLP

(57) ABSTRACT

The present invention relates to a sensor applicator assembly for a continuous glucose monitoring system and provides a sensor applicator assembly for a continuous glucose monitoring system, which is manufactured with a sensor module assembled inside an applicator, thereby minimizing additional work by a user for attaching the sensor module to the body and allowing the sensor module to be attached to the body simply by operating the applicator, and thus can be used more conveniently. A battery is built in the sensor module and a separate transmitter is connected to the sensor module so as to receive power supply from the sensor module and be continuously used semi-permanently, thereby making the assembly economical. The sensor module and the applicator are used as disposables, thereby allowing accurate and safe use and convenient maintenance.

7 Claims, 30 Drawing Sheets

(51) Int. Cl.
  *A61B 5/15* (2006.01)
  *A61B 5/155* (2006.01)
  *A61B 17/34* (2006.01)

(52) U.S. Cl.
  CPC .......... *A61B 5/14532* (2013.01); *A61B 5/155* (2013.01); *A61B 5/150244* (2013.01); *A61B 5/150847* (2013.01); *A61B 5/150969* (2013.01); *A61B 5/6832* (2013.01); *A61B 5/6848* (2013.01); *A61B 5/6849* (2013.01); *A61B 17/3468* (2013.01); *A61B 5/14503* (2013.01); *A61B 2560/0214* (2013.01); *A61B 2560/045* (2013.01); *A61B 2560/0443* (2013.01); *A61B 2560/0462* (2013.01); *A61B 2560/063* (2013.01)

(58) Field of Classification Search
  CPC ........ A61B 5/150847; A61B 5/150969; A61B 5/155; A61B 5/6832; A61B 5/6848; A61B 5/6849; A61B 5/14503; A61B 17/3468; A61B 2560/0214; A61B 2560/0443; A61B 2560/045; A61B 2560/0462; A61B 2560/063; A61M 2005/2073
  USPC ........................................................ 600/365
  See application file for complete search history.

(56) References Cited

U.S. PATENT DOCUMENTS

| | | | |
|---|---|---|---|
| 2008/0269575 | A1 | 10/2008 | Iddan |
| 2010/0211005 | A1* | 8/2010 | Edwards .................. A61P 5/28 604/82 |
| 2012/0116318 | A1* | 5/2012 | Edwards ................ G16H 20/17 604/191 |
| 2016/0058344 | A1 | 3/2016 | Peterson et al. |

FOREIGN PATENT DOCUMENTS

| | | | | |
|---|---|---|---|---|
| EP | 3 123 934 | | 2/2017 | |
| EP | 3 251 596 | | 12/2017 | |
| JP | 2008-506468 | | 3/2008 | |
| JP | 2008-237921 | | 10/2008 | |
| JP | 2010-507456 | | 3/2010 | |
| JP | 2010-531196 | | 9/2010 | |
| JP | 2013-523233 | | 6/2013 | |
| JP | 2016-128031 | | 7/2016 | |
| JP | 2017-525516 | | 9/2017 | |
| KR | 10-2017-0045236 | | 4/2017 | |
| KR | 20170045236 A | * | 4/2017 | .......... A61B 5/1473 |
| WO | 2016/120919 | | 8/2016 | |

OTHER PUBLICATIONS

Written Opinion of the International Searching Authority for PCT/KR2018/006319 dated Sep. 7, 2018 and its English translation by Google Translate (now published as WO2018/222015).

Office Action dated Dec. 15, 2020 for Japanese Patent Application No. 2019-566611 and its English translation from Global Dossier.

International Preliminary Report on Patentability (Chapter I) for PCT/KR2018/006319 dated Dec. 3, 2019 and its English translation from WIPO (now published as WO 2018/222015).

Extended European Search Report dated Mar. 9, 2021 for European Patent Application No. 18808962.7.

Notice of Allowance dated Apr. 6, 2021 for Japanese Patent Application No. 2019-566611 and its English translation from Global Dossier.

* cited by examiner

SENSOR APPLICATOR ASSEMBLY FOR CONTINUOUS GLUCOSE MONITORING SYSTEM

CROSS-REFERENCE TO RELATED APPLICATIONS

The present application is the U.S. national phase of PCT Application No. PCT/KR2018/006319, filed on Jun. 1, 2018, which claims priority to Korean Patent Application No. 10-2017-0068964, filed on Jun. 2, 2017, and Korean Patent Application No. 10-2018-0063373, filed on Jun. 1, 2018, the entire contents of which are incorporated herein by reference.

TECHNICAL FIELD

The present disclosure relates to a sensor applicator assembly for a continuous glucose monitoring system. More particularly, the present disclosure relates to a sensor applicator assembly for a continuous glucose monitoring system, in which the sensor applicator assembly is fabricated, with a sensor module being preinstalled in an applicator, so that a user can attach the sensor module to the skin by simply operating the applicator. Additional tasks of the user for attaching the sensor module to the skin can be minimized, thereby allowing the sensor applicator assembly to be more conveniently used. In addition, a battery is provided as a built-in component of the sensor module and a separate transmitter is connected to the sensor module to receive power from the sensor module, so that the transmitter can be used semi-permanently, which is economical. In addition, the sensor module and the applicator are provided to be disposable so as to be used accurately and safely, thereby allowing safe use and convenient maintenance.

BACKGROUND ART

Diabetes or diabetes mellitus is a chronic medical condition that is common in modern people. In the Republic of Korea, it affects 2 million people, about 5% of the total population.

Diabetes is caused from the absolute deficiency or relative insufficiency of insulin produced by the pancreas, due to various causes such as obesity, stress, poor eating habits, inherited hereditary factors, in which glucose balance in the blood may be disturbed, thereby resulting in a high blood sugar level.

The blood usually contains a certain concentration of glucose, and tissue cells gain energy from the glucose.

However, when the content of glucose is increased excessively, it is not properly stored in the liver, muscle, or adipose tissue and accumulates in the blood. As a result, patients with diabetes maintain a much higher blood glucose level than other people. Excessive blood glucose passes through the tissues and is discharged into the urine, resulting in deficiency of glucose, which is absolutely necessary for all tissues of the body, thereby causing abnormalities in respective body tissues.

Diabetes mellitus is characterized by substantial absence of subjective symptoms at the beginning of the condition. When diabetes mellitus progresses, diabetes-specific symptoms such as diarrhea, polyuria, weight loss, general anxiety, skin itchiness, and scarring of the hands and feet are present. Further progression of diabetes leads to complications such as visual disturbances, hypertension, kidney disease, paralysis, periodontal disease, muscle spasms and neuralgia, as well as gangrene.

Systematic blood glucose measurement and treatment should be performed to diagnose diabetes beforehand and manage the condition to prevent the progression of diabetes into complications associated therewith.

For people with diabetes or people having higher than normal blood glucose, even though diabetes has not yet developed, medical device manufacturers offer a variety of blood glucose meters to measure blood glucose levels at home.

Glucose monitoring systems are categorized on the basis of a method of measuring a blood glucose level once by a user collecting blood from a fingertip and a method of continuously measuring blood glucose levels by attaching a glucose monitoring system to the belly or an arm of a user.

Diabetics generally traverse between hyperglycemia and hypoglycemia. An emergency may occur in hypoglycemic conditions, in which diabetics may become unconscious or die if a hypoglycemic condition lasts for an extended period of time without the supply of sugar. Accordingly, rapid discovery of a hypoglycemic condition is critically important for diabetics. However, invasive glucose monitoring systems intermittently measuring glucose by collecting blood have limited ability to accurately measure blood glucose levels.

Recently, to overcome such a drawback, continuous glucose monitoring systems (CGMSs) have been developed. Such a CGMS is inserted into the body to measure a blood glucose level every few minutes. In this manner, the treatment of diabetics and measures in response to an emergency can be easily undertaken.

In addition, in an invasive glucose monitoring system, a diabetic performs glucose measurement by collecting blood by pricking a pain-sensitive fingertip with a needle. Therefore, a blood collecting process may cause pain and aversion to measurement. To minimize such pain and aversion to measurement, research and development of CGMSs have been undertaken. In such a CGMS, glucose is continuously measured by inserting a needle-shaped sensor into a portion of the human body, such as the belly or an arm, which is less pain sensitive. Furthermore, research and development of non-invasive glucose monitoring systems for measuring glucose without collecting blood have been actively undertaken.

Regarding non-invasive glucose monitoring systems, a variety of methods of measuring glucose without collecting blood have been studied over the past 40 years. Such methods may include electrical methods, exhalation measurement methods, and the like. Cygnus (Redwoo City, Ca, USA) has developed and launched the Glucowatch® G2 Biographer, a watch-shaped glucose monitoring device, using reverse iontophoresis. However, the distribution of this device was stopped in 2007, because of problems, such as skin irritation, measurement approval, and a device malfunctioning caused by excessive sweating. Although a variety of non-invasive glucose monitoring techniques have been introduced and reported to date, there have been no practical uses due to low levels of accuracy thereof.

A continuous glucose monitoring system includes: a sensor module attached to the skin of a human body to measure a blood glucose level by extracting body fluid, a transmitter transmitting the blood glucose level measured by the sensor module to a terminal, the terminal outputting the received blood glucose level, and the like. The sensor module includes, for example, a needle-shaped sensor probe for insertion into subcutaneous fat to extract interstitial fluid. A separate applicator for attaching the sensor module to the body is used.

Such continuous glucose monitoring systems are fabricated to have a wide variety of shapes depending on the manufacturer thereof, and are used in a variety of methods. However, in majority continuous glucose monitoring systems fabricated and distributed, a disposable sensor module is attached to the body using an applicator. A user should perform a multistage process to operate an applicator to attach a disposable sensor module to the body. After the sensor module is attached to the skin, the user should perform a variety of follow-up procedures by him or herself, such as a procedure of withdrawing a needle.

For example, a variety of procedures that the user should perform may include: unpacking the disposable sensor module, accurately inserting the disposable sensor module into the applicator, operating and inserting the applicator into the skin, with the sensor module being inserted into the applicator, withdrawing the needle of the sensor module from the skin using a separate device by him or herself after the insertion of the sensor module into the skin, and the like.

Accordingly, the process for measuring glucose using a continuous glucose monitoring system is significantly difficult and inconvenient, which are problematic. In addition, a transmitter used to transmit information regarding the sensor module is disposable together with the sensor module, although the transmitter is relatively expensive. Accordingly, there is another problem in that this solution is significantly inefficient in economic and environmental aspects.

DISCLOSURE

Technical Problem

Accordingly, the present disclosure has been made in consideration of the above-described problems occurring in the related art, and the present disclosure proposes a sensor applicator assembly for a continuous glucose monitoring system, in which the sensor applicator assembly is fabricated, with a sensor module being preinstalled in an applicator, so that a user can attach the sensor module to the skin by simply operating the applicator. Additional tasks of the user for attaching the sensor module to the skin can be minimized, thereby allowing the sensor applicator assembly to be more conveniently used.

Also proposed is a sensor applicator assembly for a continuous glucose monitoring system, in which a battery is provided as a built-in component of the sensor module and a separate transmitter is connected to the sensor module to receive power from the sensor module, so that the transmitter can be used semi-permanently, which is economical. In addition, the sensor module and the applicator are provided to be disposable so as to be used accurately and safely, thereby allowing safe use and convenient maintenance.

Technical Solution

The present disclosure provides a sensor applicator assembly for a continuous glucose monitoring system, the sensor applicator assembly being assembled as a single unitary product in which a sensor module periodically measuring a blood glucose level is preinstalled in an applicator, such that the sensor module is ejected by an operation of the applicator to be attached to a human body. The applicator may have a press button mounted thereon to be press-manipulated by a user. A separate safety locking device may be coupled to prevent the press button from being press-manipulated. The press button may be allowed to be press-manipulated after the safety locking device is removed.

Here, the applicator may include: a main container having an accommodation space therein and an open side, with a press button being mounted on the main container to be press-manipulated by a user; a plunger body disposed in a first position within the main container to move linearly from the first position to a second position in an ejecting direction in response to the press button being manipulated; and an elastic plunger spring applying elastic force to the plunger body so that the plunger body moves linearly from the first position to the second position. The sensor module may be coupled to the plunger body to move from the first position to the second position, integrally with the plunger body. The safety locking device may be coupled to the main container.

In addition, a button guide opening, into which the press button is inserted, may be provided in the external container, the button guide opening allowing the inserted press button to move when pressed. The safety locking device may be slid into the button guide opening in a direction perpendicular to a depth direction of the button guide opening to prevent the press button from moving when pressed.

In addition, the safety locking device may include: an anti-pressing rod configured to be inserted into and withdrawn from the button guide opening by sliding; and an outer support extending from one end of each of the anti-pressing rod and surrounds an outer circumferential surface of the external container, with the anti-pressing rod being inserted into the button guide opening. As the anti-pressing rod is inserted into the button guide opening, the press button may be prevented from moving when pressed.

In addition, the outer support may have a gripping protrusion protruding outward.

In addition, a separate protective cap may be detachably coupled to the main container to block the sensor module, inserted into the main container, from being exposed externally. When the protective cap is coupled to the main container, the safety locking device may be prevented from being decoupled from the main container.

In addition, an engagement extension may be provided on the outer support to extending perpendicularly to a sliding direction of the anti-pressing rod, such that, as the protective cap is coupled to the external container in a state in which the outer support is coupled to the external container while surrounding an outer surface of the external container, the engagement extension engages with the protective cap.

Advantageous Effects

According to the present disclosure, the sensor applicator assembly is fabricated, with the sensor module being preinstalled in the applicator, so that a user can attach the sensor module to the skin by simply operating the applicator. Additional tasks of the user for attaching the sensor module to the skin can be minimized, thereby allowing the sensor applicator assembly to be more conveniently used.

In addition, a battery is provided as a built-in component of the sensor module and the separate transmitter is connected to the sensor module to receive power from the sensor module, so that the transmitter can be used semi-permanently, which is economical. In addition, the sensor module and the applicator are provided to be disposable so as to be used accurately and safely, thereby allowing safe use and convenient maintenance.

In addition, at the moment that the sensor module is attached to the human body by the operation of the applicator, the needle is automatically removed. Accordingly, it is possible to rapidly remove the needle without pain without causing the human body to be injured during the removal of the needle, thereby further improving the convenience of use.

In addition, a release paper is removed from the sensor module while a protective cap is being detached, so that the sensor module can be attached to the human body with no other additional tasks, except for the operation of detaching the protective cap.

In addition, since the applicator cannot be reused after having been operated, it is possible to prevent a user from using the applicator improperly, thereby enabling the applicator to be used more safely.

MODE FOR INVENTION

Figure 1:
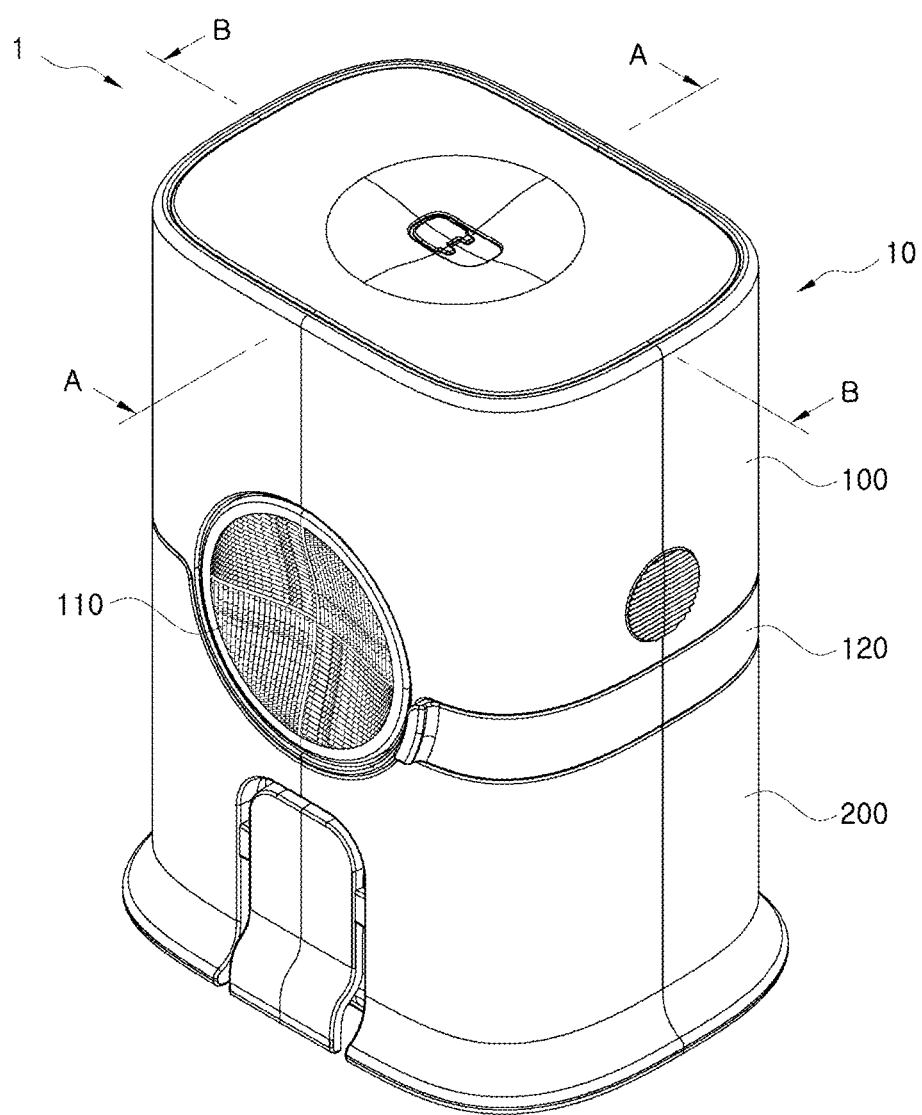
FIG. 1 is a perspective view schematically illustrating an assembled configuration of a sensor applicator assembly for a continuous glucose monitoring system according to embodiments of the disclosure.

Hereinafter, embodiments of the present disclosure will be described in detail with reference to the accompanying drawings. Throughout this document, reference should be made to the drawings, in which the same reference numerals and symbols will be used to designate the same or like components. In the following description of the present disclosure, detailed descriptions of known functions and components incorporated herein will be omitted in the case that the subject matter of the present disclosure may be rendered unclear thereby.

Figure 2:
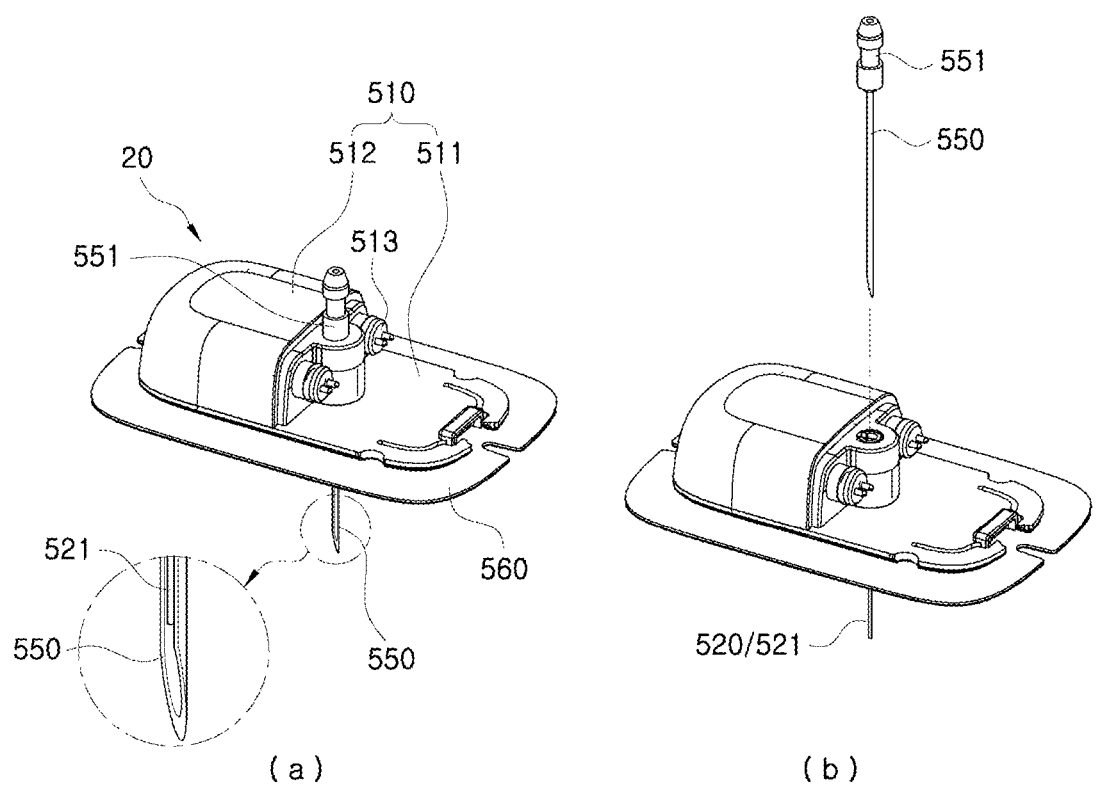
FIG. 2 is a perspective view schematically illustrating a configuration of a sensor module according to embodiments of the disclosure.
Figure 3:
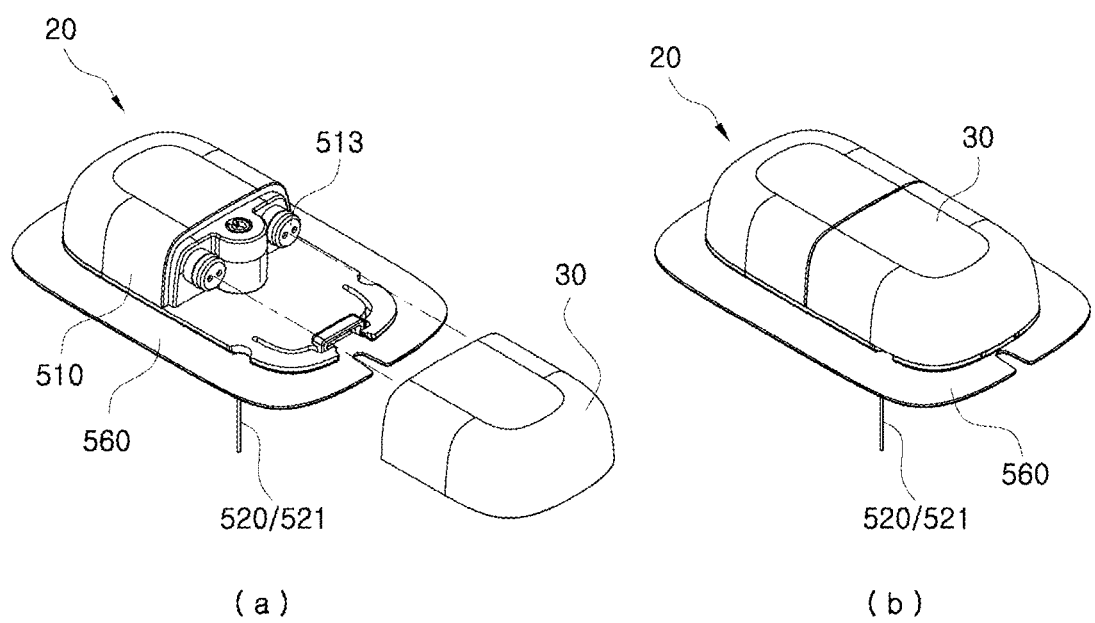
FIG. 3 is a perspective view illustrating an operation of attaching a transmitter to the sensor module according to embodiments of the disclosure.
Figure 4:
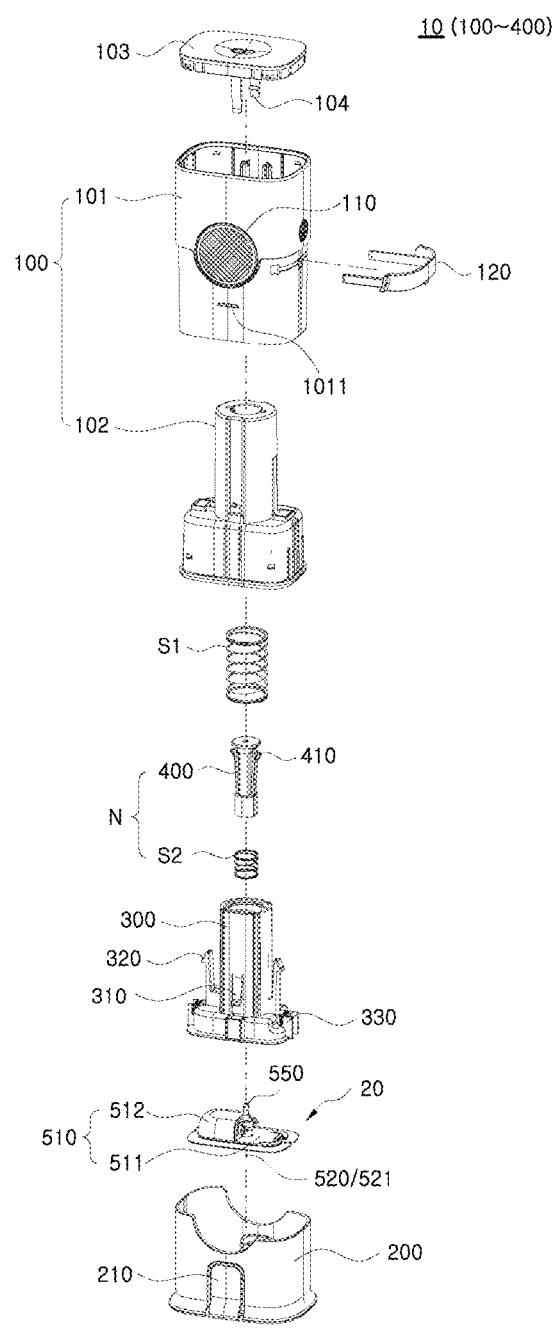
FIG. 4 is an exploded perspective view schematically illustrating the sensor applicator assembly for a continuous glucose monitoring system according to embodiments of the disclosure.
Figure 5:
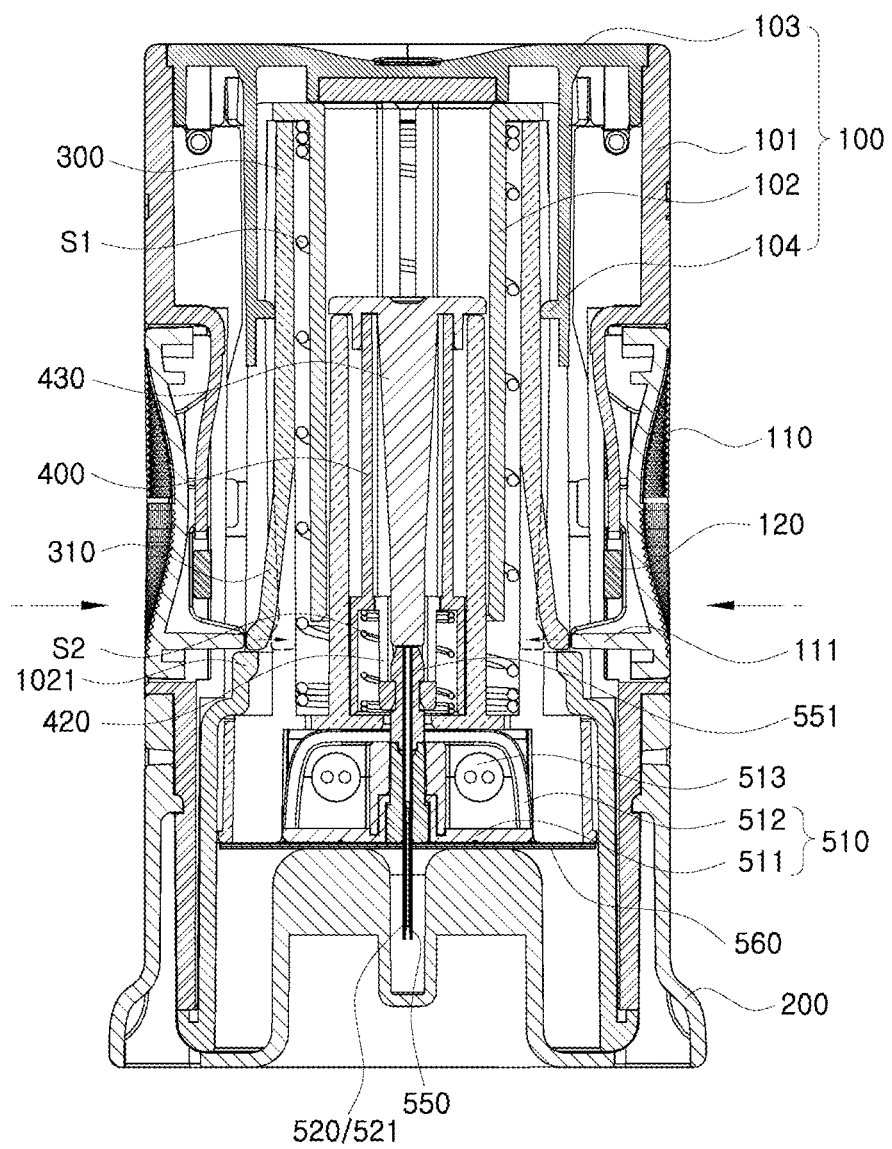
FIG. 5 is a cross-sectional view taken along line A-A in FIG. 1.
Figure 6:
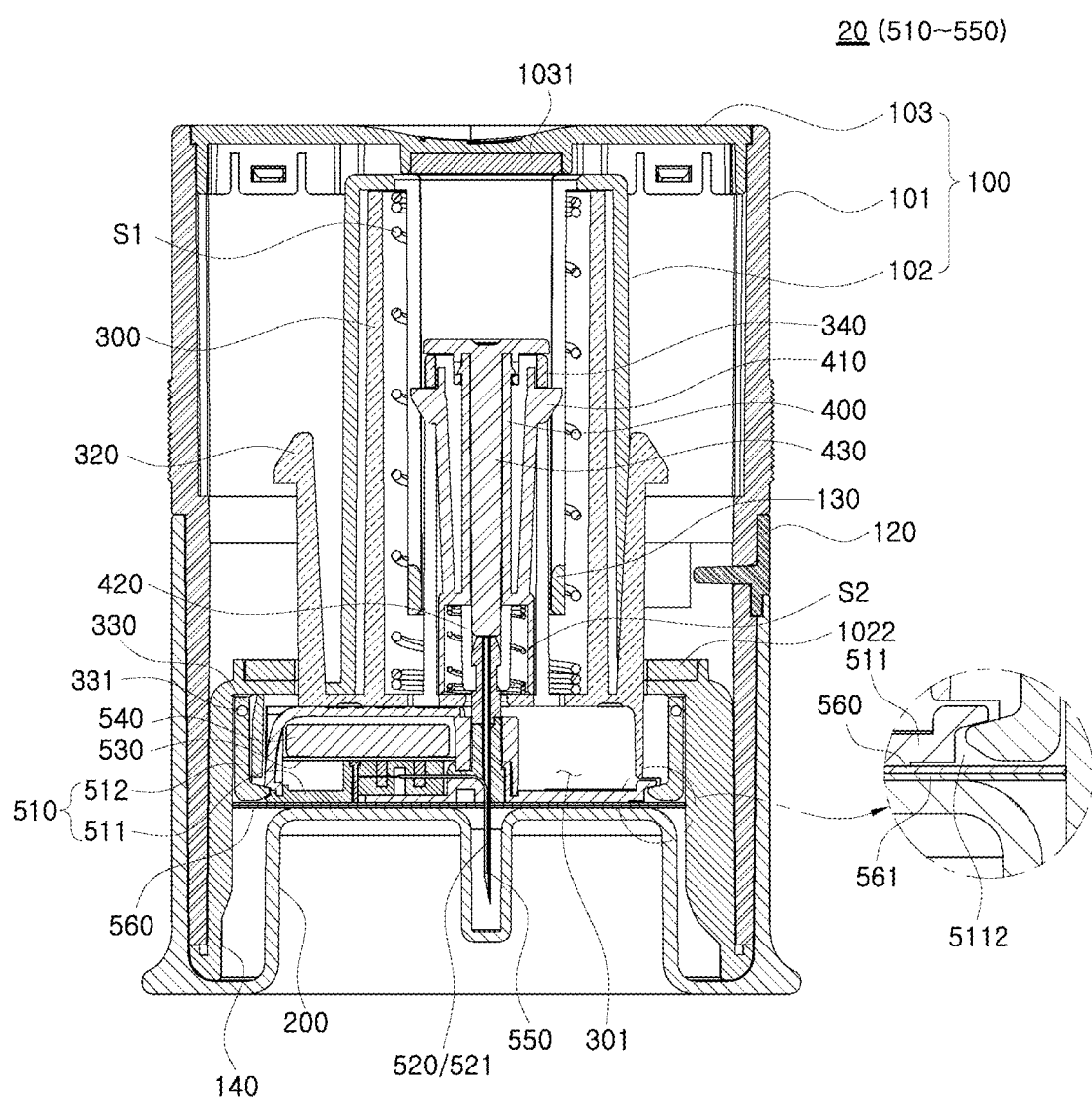
FIG. 6 is a cross-sectional view taken along line B-B in FIG. 1.

FIG. 1 is a perspective view schematically illustrating an assembled configuration of a sensor applicator assembly for a continuous glucose monitoring system according to embodiments of the disclosure, FIG. 2 is a perspective view schematically illustrating a configuration of a sensor module according to embodiments of the disclosure, FIG. 3 is a perspective view illustrating an operation of attaching a transmitter to the sensor module according to embodiments of the disclosure, FIG. 4 is an exploded perspective view schematically illustrating the sensor applicator assembly for a continuous glucose monitoring system according to embodiments of the disclosure, FIG. 5 is a cross-sectional view taken along line A-A in FIG. 1, and FIG. 6 is a cross-sectional view taken along line B-B in FIG. 1.

The sensor applicator assembly 1 for a continuous glucose monitoring system according to embodiments of the disclosure is an assembly fabricated as a single unitary product by fitting a sensor module 20 and an applicator 10 together. The sensor applicator assembly 1 has a structure to be use thereof to be very simple, thereby minimizing additional tasks of a user to use the continuous glucose monitoring system.

The sensor module 20 is configured to be attachable to a portion of the human body to extract body fluid and periodically measure a blood glucose level, and allows a separate transmitter 30 to be connected thereto to transmit a glucose measurement result to an external device, such as a mobile device (not shown).

The applicator 10 is configured such that the sensor module 20 is fixedly coupled to an inner portion thereof, and operates to eject the sensor module 20 in response to a user's manipulation.

Here, fabrication and assembly processes are performed, with the sensor module 20 being preinstalled in the applicator 10. When the applicator 10 is operated by the user's manipulation, the sensor module 20 is moved in an ejecting direction to be attached to the portion of the human body.

That is, the sensor applicator assembly 1 according to embodiments of the disclosure is assembled and fabricated in a fabrication process, with the sensor module 20 being preinstalled in the applicator, such that the sensor module 20 is attachable to the skin only by the operation of the applicator 10. The sensor applicator assembly 1 is provided to a user in this state. Accordingly, the user can attach the sensor module 20 to the skin by simply operating the applicator 10 without an additional operation for attaching the sensor module 20 to the skin. After the sensor module 20 is attached to the skin, the separate transmitter 30 is connected to the sensor module 20, so that a glucose measurement result can be periodically output from a terminal of the continuous glucose monitoring system.

When the lifetime of the sensor module 20 has ended after having been used for about one (1) week while attached to the human body, a new sensor module 20 must be attached to the human body. Here, the sensor module 20 and the applicator 10 are fabricated and used to be disposable, while the transmitter 30 is continuously used as a separate product. That is, since the sensor module 20 is distributed as being preinstalled in the applicator 10 and attachable to the human body, an additional operation of, for example, inserting the sensor module 20 into the applicator 10 by the user is unnecessary. The user attaches the sensor module 20 to the body by simply operating the applicator 10. After the sensor module 20 and the applicator 10 have been used in this manner, the sensor module 20 and the applicator 10 cannot be reused. A new sensor module 20 is attached to the body using a new sensor applicator assembly 1. Here, the transmitter 30 may be configured to be reusable as a separate product instead of being disposable.

In a typical continuous glucose monitoring system of the related art, a sensor module separately packed is unpacked and then is accurately inserted into an applicator. After the insertion, the applicator is operated to attach the sensor module to the skin. The operation of accurately insert the sensor module into the applicator is bothering and difficult. Children or older persons may contaminate the sensor module during this operation, thereby lowering the accuracy of measurement, which is problematic.

According to embodiments of the disclosure, the sensor module 20 is preinstalled in the applicator 10 in the fabrication process, so that the applicator 10 is distributed with the sensor module 20 preinstalled therein. The user's operations of, for example, unpacking the sensor module 20 and inserting the sensor module 20 into the applicator 10 may be omitted. It is possible to attach the sensor module 20 to the skin by simply manipulating the applicator 10. Accordingly, the usability of the sensor module 20 can be significantly improved, and in particular, the contamination of the sensor module 20 or the like can be prevented, thereby improving the accuracy of glucose measurement.

Since the sensor module 20 is preinstalled in the applicator 10 in the fabrication process as described above, the sensor module 20 and the applicator 10 may be provided to be disposable so as not to be reusable. To provide such a disposable structure, the applicator 10 according to embodiments of the disclosure is configured such that the sensor module 20 cannot be reinserted into the applicator 10 after the applicator 10 is operated once to eject the sensor module 20 therefrom.

That is, the applicator 10 is configured to have one open side, through which the sensor module 20 is ejected to the outside. The applicator 10 may be configured such that, once the applicator 10 has ejected the sensor module 20 by an initial single operation, another sensor module 20 is prevented from being inserted into the applicator 10, so that the user cannot insert the sensor module 20 into the applicator 10.

In addition, a separate protective cap 200 may be detachably coupled to the applicator 10 to prevent the sensor module 20, preinstalled in the applicator 10, from being exposed externally. The protective cap 200 may be configured such that the user cannot attach the sensor module 20 to the human body by operating the applicator 10 unless the protective cap 200 is detached.

Here, adhesive tape 560 is attached to a body contact surface of the sensor module 20, such that sensor module 20 can be attached to the human body. A release paper 561 is attached to the body contact surface of the adhesive tape 560 to protect the adhesive tape 560. The release paper 561 of the adhesive tape 560 may be detached and removed from the adhesive tape 560 while the protective cap 200 is being detached from the applicator 10.

For example, the release paper 561 may be configured such that one portion thereof is bonded to the protective cap 200. Thus, when the user detaches the protective cap 200 from the applicator 10, the release paper 561 can be detached and removed from the adhesive tape 560 along with the protective cap 200. Accordingly, when the user detaches the protective cap 200, the release paper 561 is removed from the adhesive tape 560. In this state, it is possible to attach the sensor module 20 to the human body by operating the applicator 10.

In addition, the applicator 10 may be configured such that, in a state in which the sensor module 20 is preinstalled in the applicator 10, the sensor module 20 is fixedly coupled to the applicator 10, and in a state in which the sensor module 20 is ejected (i.e. is moved outwardly by ejection), the sensor module 20 is decoupled from the applicator 10. Thus, in a state in which the sensor module 20 is inserted into and coupled to the applicator 10, the sensor module 20 remains in a fixed position. In a state in which the sensor module 20 is ejected to be attached to the skin by operating the applicator 10, the sensor module 20 is decoupled from the applicator 10. In this situation, when the applicator 10 is detached from the skin, the applicator 10 and the sensor module 20 are detached from each other, while the sensor module 20 remains attached to the skin.

Next, respective specific configurations will be described in more detail.

Figure 7:
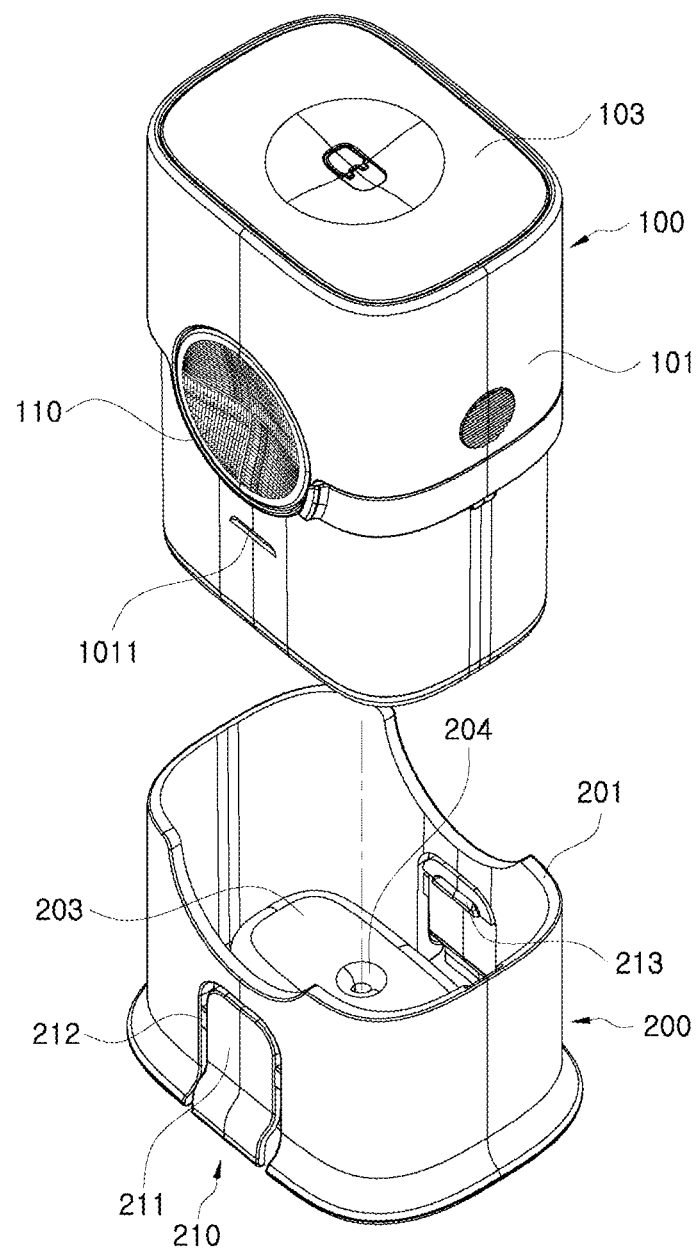
FIG. 7 is a perspective view schematically illustrating a configuration of the protective cap according to embodiments of the disclosure.

First, the protective cap 200 is detachably coupled to the open side of the applicator 10 to prevent the sensor module 20, preinstalled in the applicator 10, from being exposed externally. The protective cap 200 is provided with locking members 210 to prevent the protective cap 200, coupled to the applicator 10, from being detached from the applicator 10, as illustrated in FIG. 7. The locking members 210 are configured to be locked or unlocked by the user's manipulation.

Each of the locking members 210 includes a locking lever 211 pivotably coupled to one side of the protective cap 200 and a locking catch protrusion 213 provided on one end of the locking lever 211. The locking lever 211 may have an elastic hinge shaft 212 provided on an intermediate portion thereof, such that both end portions of the locking lever 211 elastically pivot about the elastic hinge shaft 212. In addition, locking catch recesses 1011 corresponding to the shape of the locking members 210 may be formed in outer circumferential portions of the applicator 10, such that the locking catch protrusion 213 may be fitted into and engaged with the locking catch recesses 1011.

Here, the locking lever 211 may be configured to be elastically supported by the elastic hinge shaft 212 in a direction in which the locking catch protrusion 213 is fitted into and engaged with the locking catch recesses 1011.

Figure 8A:
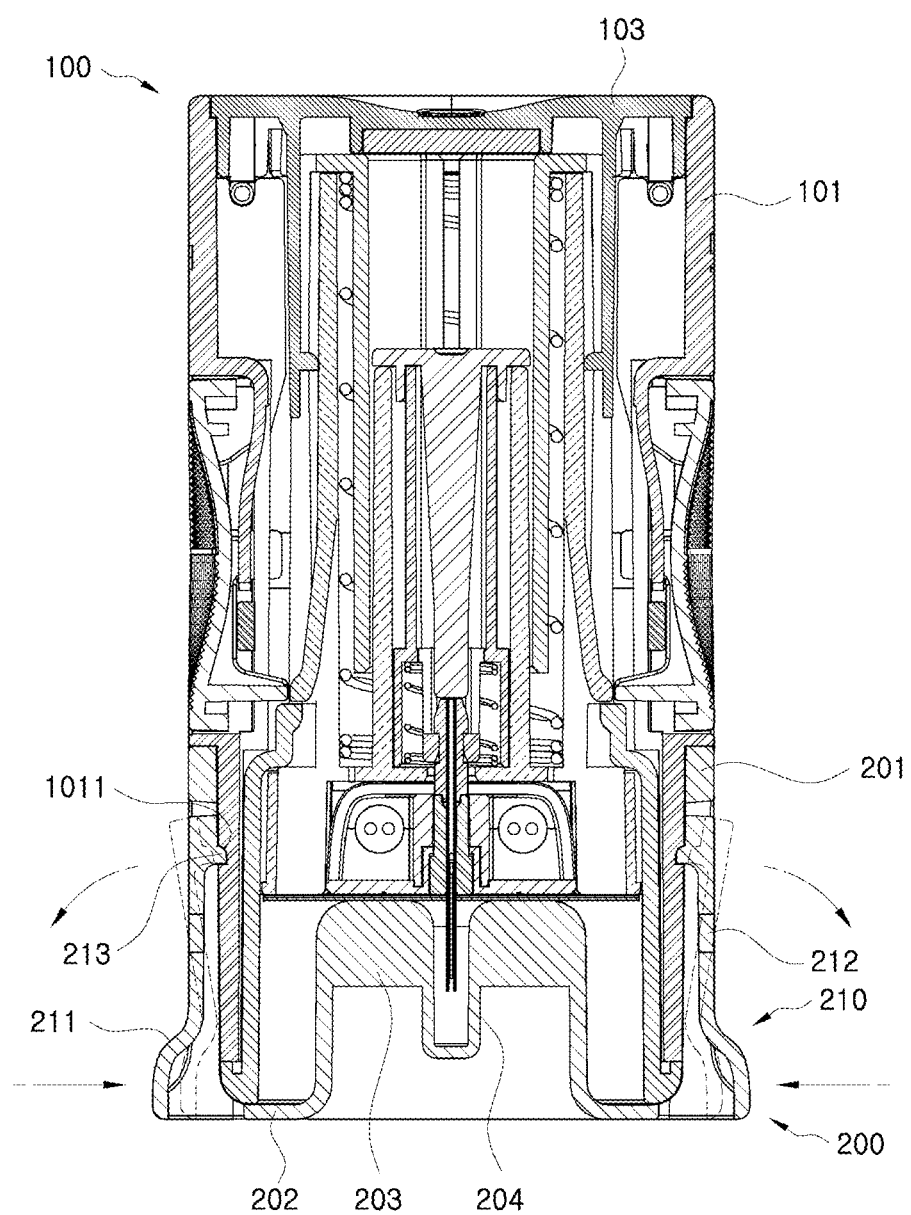
FIGS. 8A and 8B are views illustrating a process of removing the protective cap according to embodiments of the disclosure.
Figure 8B:
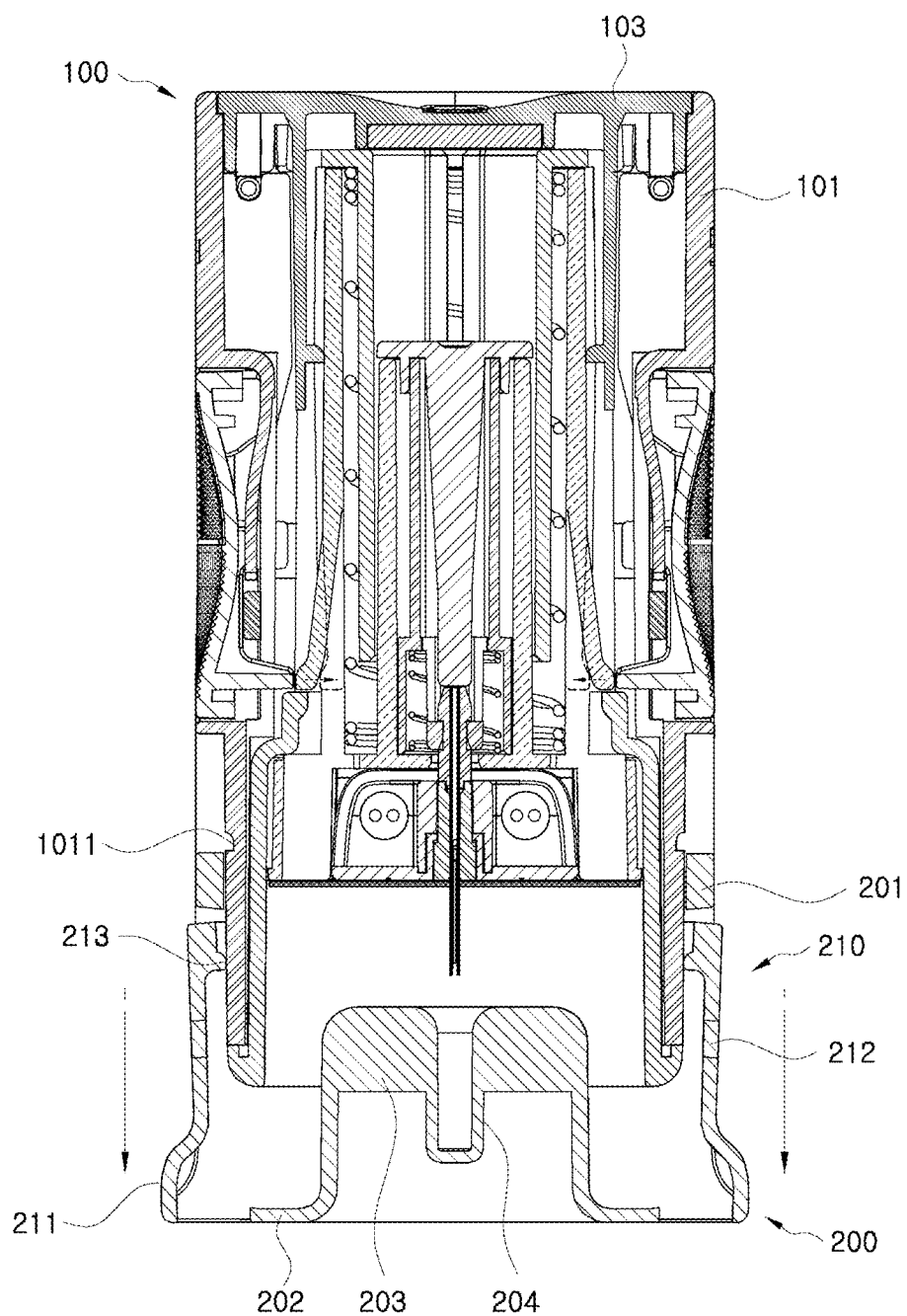

According to this configuration, the protective cap 200 remains coupled to the applicator 10 unless the user presses the bottom end portion of the locking lever 211, as illustrated in FIG. 8a. In a state in which the locking catch protrusion 213 is disengaged from the locking catch recesses 1011 by pressing the locking lever 211, the protective cap 200 can be detached and removed from the applicator 10, as illustrated in FIG. 8b.

The protective cap 200 includes an outer cover 201, an extension 202, and an inner support 203. The outer cover 201 is coupled to one end portion of the applicator 10, and surrounds, while being in contact with, an outer circumferential surface of the applicator 10. The extension 202 extends from one end of the outer cover 201 in the direction of the inner center of the applicator 10. The inner support 203 extends upward from the extension 202 to support the body contact surface of the sensor module 20 preinstalled in the applicator 10. Here, a sensor protector 204 may protrude downward from a local portion the central portion of the inner support 203 to surround a sensor probe 521 and a needle 550 protruding downward from the body contact surface of the sensor module 20.

Accordingly, the protective cap 200 not only blocks the sensor module 20, preinstalled in the applicator 10, from being exposed externally, but also supports the sensor module 20. The protective cap 200 generally improves the structural stability of the sensor applicator assembly.

In addition, as described above, the adhesive tape 560 and the release paper 561 are attached to the body contact surface of the sensor module 20. In the process of detaching the protective cap 200 from the applicator 10, the release paper 561 of the adhesive tape 560 is detached and removed from the adhesive tape 560 along with the protective cap 200.

Figure 9A:
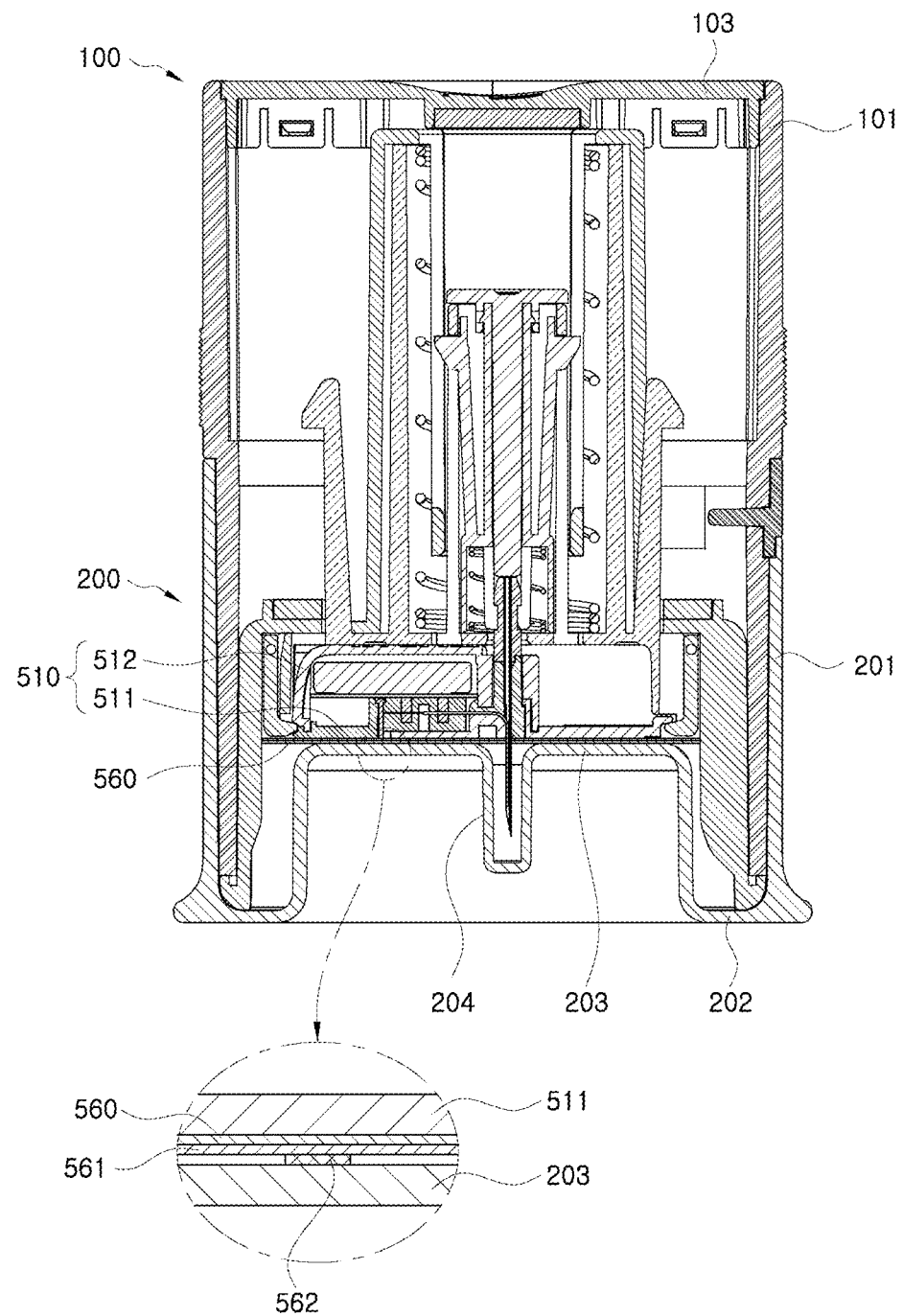
FIGS. 9A and 9B are views illustrating a process of removing the release paper together with the protective cap according to embodiments of the disclosure.

Here, the release paper 561 may be attached to the top surface of the inner support 203 of the protective cap 200, and may be attached to the inner support 203 of the protective cap 200 via a separate adhesive member 562. That is, as illustrated in FIG. 9a, a separate adhesive member 562 is bonded to a bottom surface portion of the release paper 561. The adhesive member 562 is located between the top surface of the inner support 203 of the protective cap 200 and the release paper 561, such that the bottom surface of the adhesive member 562 is bonded to the top surface of the inner support 203. The bonding force of the adhesive member 562 is set to be greater than the bonding force between the release paper 561 and the adhesive tape 560. Thus, when the protective cap 200 is detached from the applicator 10, the release paper 561 bonded to the inner support 203 of the protective cap 200 via the adhesive member 562 is detached from the inner support 203 along with the protective cap 200. In this manner, the release paper 561 is detached and removed from the adhesive tape 560.

Figure 9B:
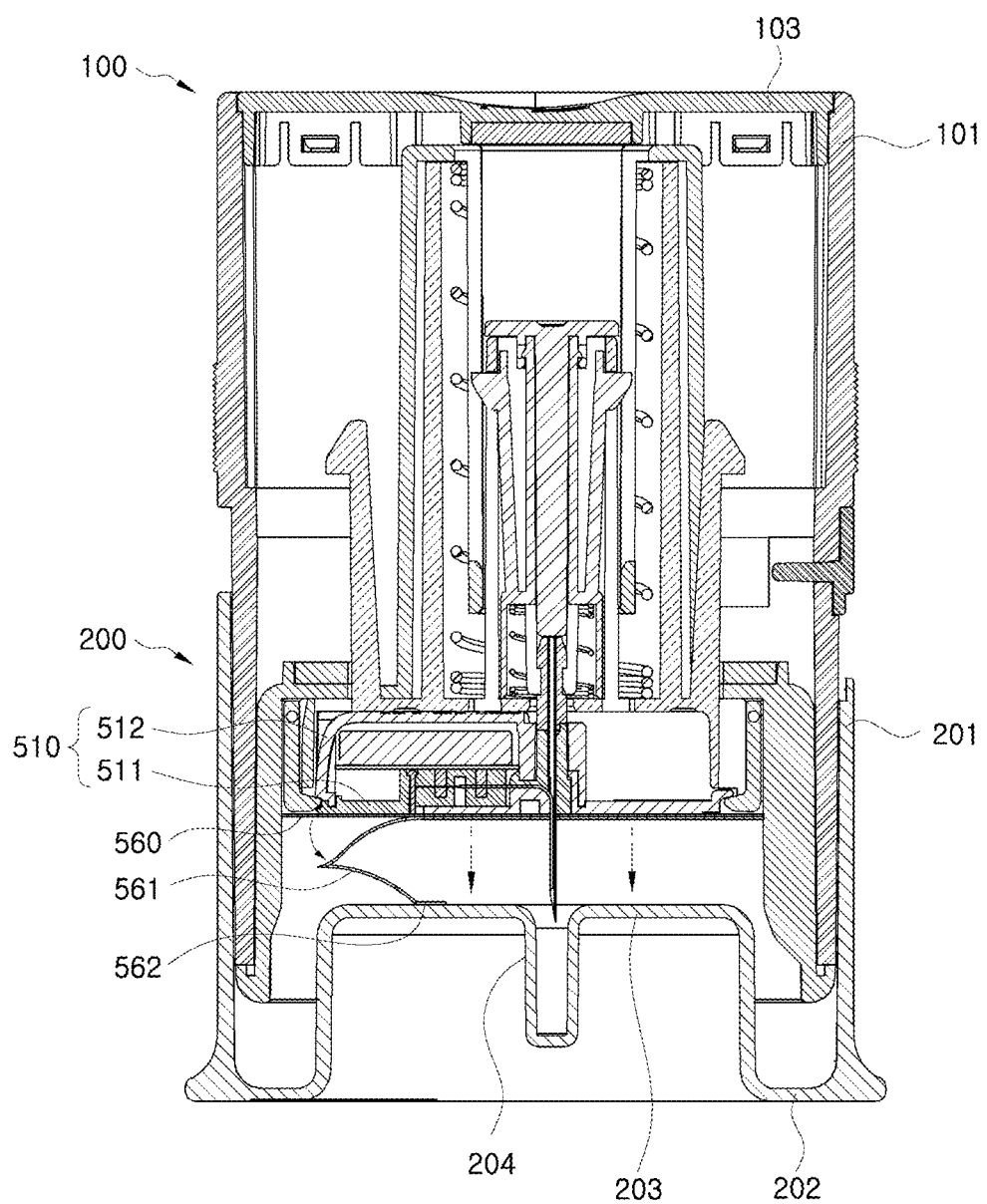
Figure 10:
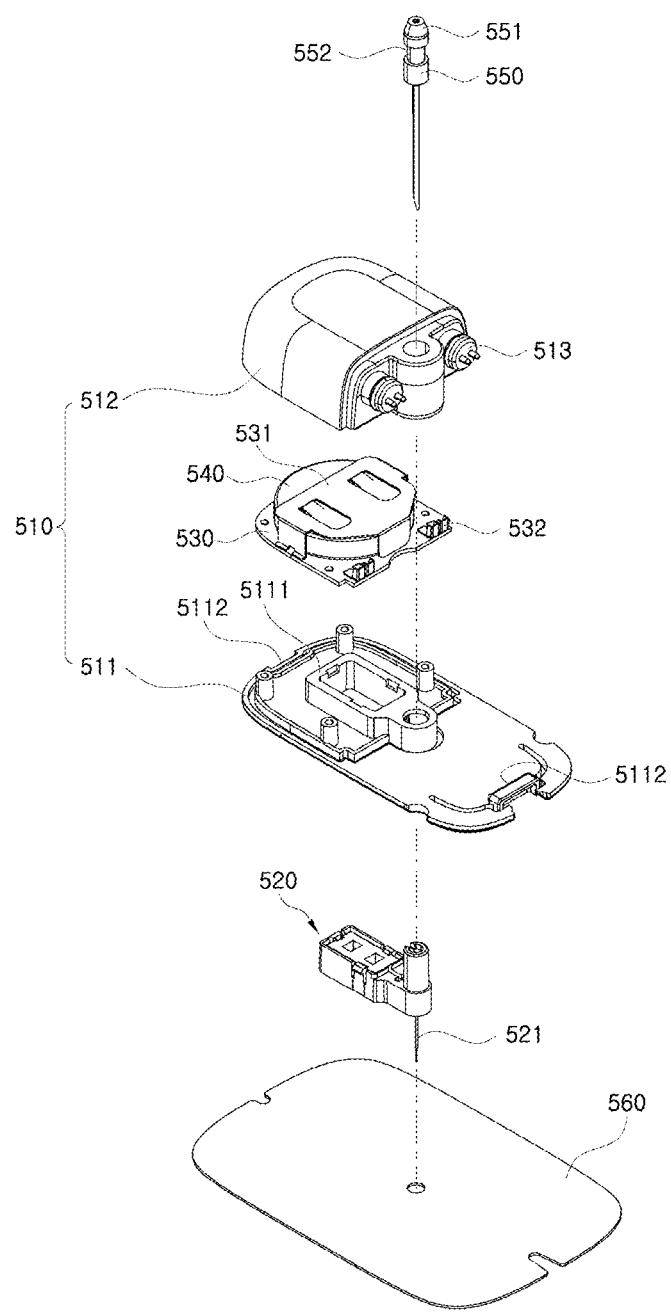
FIG. 10 is an exploded perspective view schematically illustrating a specific configuration of the sensor module according to embodiments of the disclosure.
Figure 11:
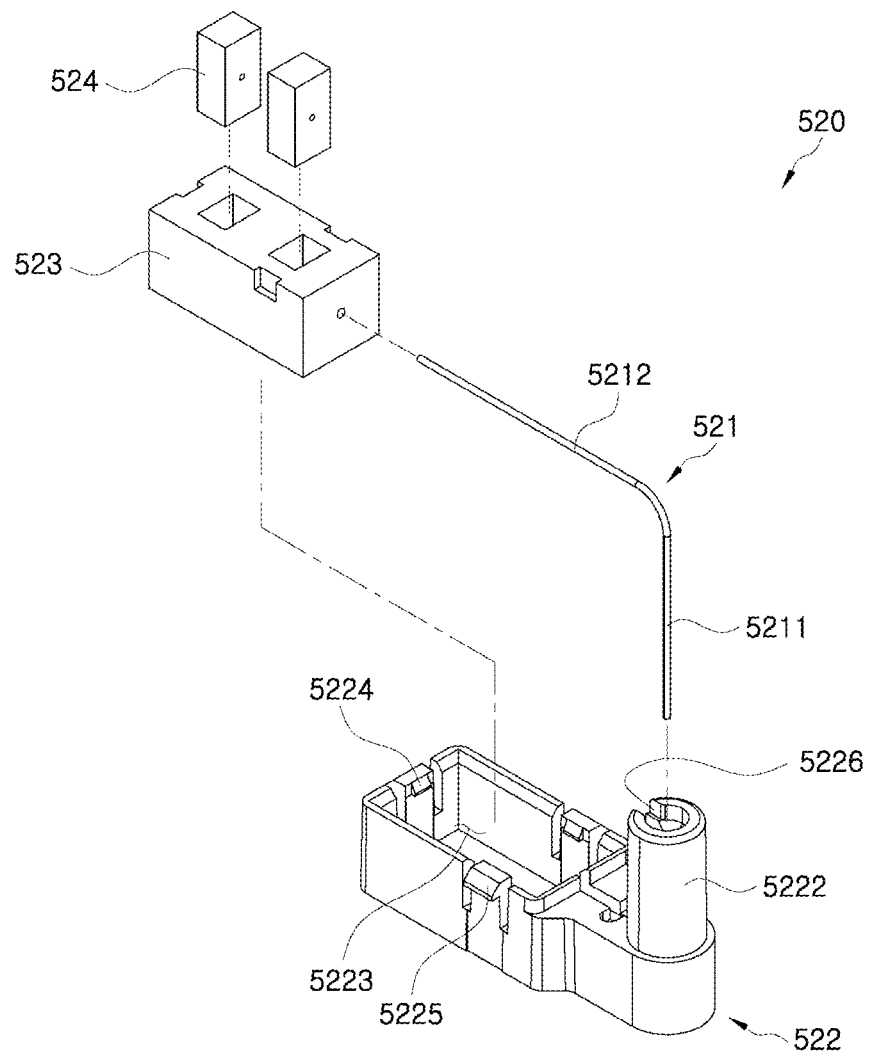
FIG. 11 is an exploded perspective view schematically illustrating a configuration of the sensor of the sensor module according to embodiments of the disclosure.
Figure 12:
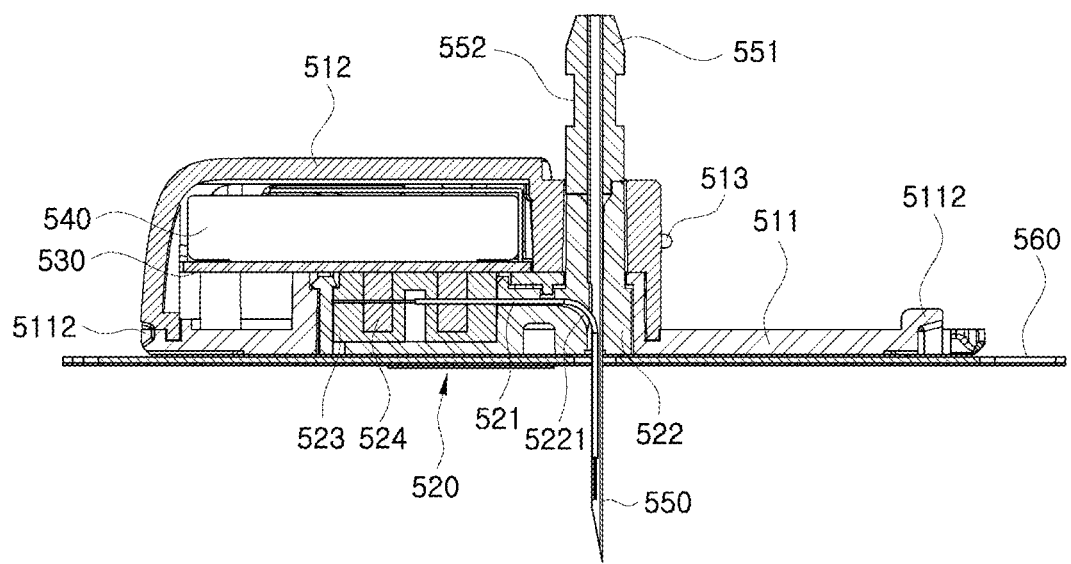
FIG. 12 is a cross-sectional view schematically illustrating an internal configuration of the sensor module according to embodiments of the disclosure.

Here, two parallel cutting lines (not shown) having the same width and size as those of the adhesive member 562 may be formed in portions of the release paper 561. Consequently, as illustrated in FIG. 9b, first, in the process of detaching the protective cap 200, the release paper 561 is detached from the adhesive tape 560 along the cutting lines along with the adhesive member 562. Afterwards, in response to continued detaching of the protective cap 200, i.e. continued downward movement of the protective cap 200 respect to the direction illustrated in FIG. 9b, the release paper 561 in portions other than the cutting line is pulled, thereby being detached and removed from the adhesive tape 560. Due to this release paper detaching process, the operation of detaching and removing the release paper 561 can be more easily and reliably performed.

In addition, the above-described locking levers 211 of the protective cap 200 may be provided on the central portions of the outer cover 201. For example, the locking lever 211 may be provided such that the locking lever 211 is formed by cutting a portion of the outer cover 201 and the elastic hinge shaft 212 is formed on a portion cutting lines to be connected to the outer cover 201.

The sensor module 20 includes a pod 510, a sensor 520, a printed circuit board (PCB) 530, and a battery 540.

The adhesive tape 560 is attached to the bottom end surface of the pod 510, such that the sensor module 20 can be ejected by the applicator 10 so as to be attached to the human body. The pod 510 has a connector terminal 513 to which the transmitter 30 can be connected. The pod 510 may include a flat plate-shaped pod base 511 and a case-shaped pod body 512. The adhesive tape 560 is attached to the bottom end surface of the pod base 511. The pod body 512 is provided on a portion of the top surface of the pod base 511 to surround a portion of a space above the pod base 511. The pod body 512 is located on a top surface portion of the pod base 511. The sensor 520, the PCB 530, the battery 540, and the like, are disposed in the internal space of the pod body 512. The pod 510 is attached to the human body by the operation of the applicator 10. The pod base 511 is attached to the human body via the adhesive tape 560. Afterwards, the separate transmitter 30 is seated on and coupled to the top surface of the pod base 511 so as to be connected to the connector terminal 513 of the pod body 512.

The sensor 520 is disposed within the internal space of the pod 510 such that one end portion of the sensor 520 protrudes downward from the pod 510. As the pod 510 is ejected, the one end of the sensor 520 is inserted into the body to extract blood and measure a blood glucose level. The sensor 520 includes a sensor probe 521 having one end portion protruding downward from the bottom end surface of the pod base 511, the sensor probe 521 being able to be inserted into the body to extract blood.

The PCB 530 is disposed within the internal space of the pod 510, and is electrically connected to the other end portion of the sensor probe 521. One end portion of the sensor probe 521 is inserted into the skin to react with glucose in the body fluid. Here, current change information of the sensor probe 521 occurring depending on the glucose concentration of blood is electrically transferred to the PCB 530. The PCB 530 has a terminal connector point 532 to be connected to the connector terminal 513 provided on the pod 510.

The battery 540 is disposed on the PCB 530 within the internal space of the pod 510 to supply power to the sensor 520 or the like. The PCB 530 includes a battery bracket 531 on which the battery 540 can be mounted and supported. Power supplied by the battery 540 is supplied to the connector terminal 513 via the PCB 530. In a state in which the transmitter 30 is connected to the connector terminal 513 of the pod 510, the power is supplied to the transmitter 30 via the connector terminal 513. That is, the transmitter 30 operates by receiving power from the battery 540 disposed inside of the sensor module 20. In addition, the current change information obtained using the sensor 520 is also transferred to the transmitter 30 via the PCB 530 and the connector terminal 513, and then, is transmitted to a user terminal via the transmitter 30. In addition, since the transmitter 30 operates by receiving power from the battery 540 of the sensor module 20, no separate battery is required to be disposed inside of the transmitter 30. Accordingly, the replacement of the transmitter 30 due to the power exhaustion of the battery is not required, and the transmitter 30 can be used semi-permanently.

At the moment that the pod 510 is attached to the human body after having been moved in the ejecting direction in response to the operation of the applicator 10, one end portion of the sensor 520 is inserted into the body. The sensor 520 generates a different current value depending on the glucose concentration in blood through reaction with the body fluid. Such current change information is transferred to the PCB 530, is applied to the transmitter 30 via the PCB 530 and the connector terminal 513, and is transmitted to the user terminal via the transmitter 30.

In addition, the sensor module 20 may further include the separate needle 550 to facilitate the insertion of the sensor probe 521 into the body. The needle 550 is detachably coupled to the pod 510. The needle 550 is configured to be inserted into the body together with the sensor probe 521 while surrounding one end portion of the sensor probe 521 in response to the pod 510 being ejected, so that one end portion of the sensor probe 521 is reliably inserted into the body.

As illustrated in FIG. 2, the needle 550 is detachably disposed in the pod 510 while extending through the pod 510 in the top-bottom direction. The needle 550 has the shape of a hollow pipe surrounding the sensor probe 521, and a needle head 551 is provided on the top end portion of the needle 550. When the pod 510 is moved in the ejecting direction by the applicator 10, the needle 550 is inserted into the body prior to the sensor probe 521 to assist in reliable insertion of the sensor probe 521 into the skin. The needle head 551 has a coupling recess 552 that can be coupled to the applicator 10 when withdrawing the needle 550 from the skin.

At the moment that the ejection movement of the pod 510 is completed, the applicator 10 is operable to withdraw and remove the needle 550 from the body. Accordingly, in a state in which the pod 510 is attached to the human body, the sensor probe 521 remains inserted into the body, but as illustrated in FIG. 2 (b), the needle 550 is withdrawn and removed. In this state, the transmitter 30 is coupled to the pod 510 to be connected to the connector terminal 513, as illustrated in FIGS. 3 (a) and (b).

Describing the configuration of the sensor 520 in more detail, the sensor 520 includes the sensor probe 521, a sensor housing 522, a rubber block 523, and an elastic contact 524. The sensor probe 521 is configured to be inserted into the body to extract blood, with one end portion 5211 protruding downward from the bottom end surface of the pod base 511, and the other end portion 5212 being disposed in the internal space of the pod 510. The sensor housing 522 is configured to surround a portion of the sensor probe 521 to support the sensor probe 521. The rubber block 523 is coupled to the sensor housing 522, such that the other end portion 5212 of the sensor probe 521 extends through the rubber block 523. The elastic contact 524 is inserted into the rubber block 523, such that the other end portion 5212 of the sensor probe 521 extends through the elastic contact 524. One end portion of the elastic contact 524 is in elastic contact with the PCB 530.

The sensor probe 521 is configured such that one end portion 5211 and the other end portion 5212 are bent perpendicularly from each other. The sensor housing 522 is provided with a probe passage 5221, with the sensor probe 521 being inserted into and extending through the probe passage 5221. The position of the sensor probe 521 is guided by the probe passage 5221. A needle support 5222 protrudes upward from the top portion of the sensor housing 522, such that the needle 550 is fitted to, while extending through, the needle support 5222. The sensor housing 522 is provided with a rubber receptacle 5223 on one side of the needle support 5222, such that the rubber block 523 is inserted into and accommodated in the rubber receptacle 5223. A rubber fixing hook 5224 and sensor fixing hooks 5225 are provided on sidewalls of the rubber receptacle 5223. The rubber fixing hook 5224 is engaged with the rubber block 523 to fix the rubber block 523. The sensor fixing hooks 5225 cause the sensor housing 522 to be fitted into the pod 510 by engagement. A sensor housing receptacle 5111 is provided in the pod base 511 of the pod 510. The sensor housing receptacle 5111 accommodates the sensor housing 522 inserted into and coupled to the sensor housing receptacle 5111. The sensor fixing hooks 5225, provided on the rubber receptacle 5223 of the sensor housing 522, are configured to engage with the sensor housing receptacle 5111 of the pod base 511.

The PCB 530 is disposed above the sensor 520, and the battery 540 is mounted on the top surface of the PCB 530. In the sensor probe 521 of the sensor 520, one end portion 5211 is inserted into the skin, and the other end portion 5212 is coupled to, while extending through, the rubber block 523 and the elastic contact 524. The elastic contact 524 is in electrical contact with the PCB 530. Thus, the sensor probe 521 is electrically connected to the PCB 530 via the elastic contact 524.

In addition, the needle 550 has the shape of a pipe surrounding an external space of the sensor probe 521, and extends through the needle support 5222 of the sensor housing 522 in the top-bottom direction. The needle head 551 is provided on the top end portion of the needle 550. Here, the sensor housing 522 and the needle head 551 may be provided with a guide recess 5226 and a guide protrusion 553 in a corresponding manner. The guide protrusion 553 may be inserted into the guide recess 5226 to guide a coupling position of the sensor housing 522 and the needle head 551.

Figure 13:
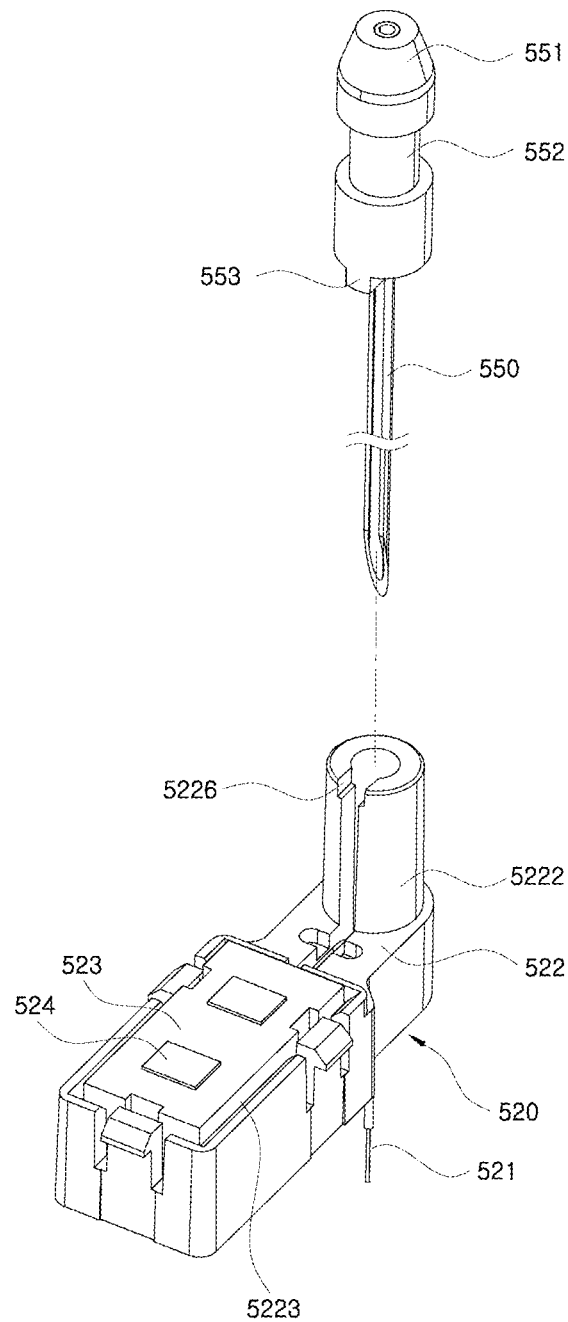
FIG. 13 is a view illustrating a coupling-guiding state of the sensor and the needle of the sensor module

For example, as illustrated in FIG. 13, the guide recess 5226 may be formed in the top end portion of the needle support 5222 of the sensor housing 522, while the guide protrusion 553 may protrude from the bottom end portion of the needle head 551 to be inserted into the guide recess 5226. Accordingly, the direction of the insertion of the needle head 551 and sensor housing 522 of the needle 550 into the sensor housing 522 may be guided so that the needle 550 and the sensor probe 521 may be coupled to each other while being accurately aligned.

The applicator 10 includes a main container 100, a plunger body 300, and an elastic plunger spring S1. The main container 100 has a press button 110 mounted on a portion of the main container 100 to be press-manipulated by a user. The plunger body 300 is fixedly coupled to an internal position, i.e. a first position, of the main container 100. In response to the press button 110 being manipulated, the plunger body 300 is decoupled from the first position to move linearly to a second position in an ejecting direction. The elastic plunger spring S1 applies elastic force to the plunger body 300 so that the plunger body 300 moves linearly from the first position to the second position. The sensor module 20 is coupled to one end portion of the plunger body 300 to move from the first position to the second position, integrally with the plunger body 300.

The main container 100 may be divided into an external container 101 and an internal container 102. The press button 110 is mounted on the external container 101. The internal container 102 is coupled to the interior of the external container 101 to guide the plunger body 300 along a linear movement path. In addition, the external container 101 may have the shape of a pipe, with a separate container cover 103 being coupled to the top end portion of the external container 101. The container cover 103 may be provided with anti-return hooks 104, as illustrated in FIGS. 4 and 5, to prevent the plunger body 300 from returning to the first position after having moved linearly to the second position.

In addition, as illustrated in FIGS. 4 and 5, a separate safety locking device 120 may be coupled to the external container 101 to prevent the press button 110 from being press-manipulated. The press button 110 can be press-manipulated after the safety locking device 120 is removed.

When a user erroneously manipulates the press button 110 by pressing it in a state in which the applicator 10 is not located in a proper position, the sensor module 20 located inside of the main container 100 is triggered and ejected. The safety locking device 120 can be mounted to prevent the sensor module 20 from being erroneously ejected, thereby enabling more reliable use.

The elastic plunger spring S1 applies elastic force to the plunger body 300 to move linearly from the first position to the second position within the main container 100. The plunger body 300 is provided with elastic hooks 310 that are elastically deformable. When the plunger body 300 is in the first position, the elastic hooks 310 may be engaged with the internal container 102 to be fixed in position. The internal container 102 is provided with fixing stepped portions 1021, with which the elastic hooks 310 of the plunger body 300 are engaged in the first position.

When the press button 110 of the external container 101 is press-manipulated inwardly as illustrated in FIG. 5, internal pressing protrusions 111 of the press button 110 press the elastic hooks 310 of the plunger body 300. This disengages the elastic hooks 310 from the internal container 102, so that the plunger body 300 is moved linearly to the second position by the elastic force of the elastic plunger spring S1. Here, as described above, it is not possible to press-manipulate the press button 110 unless the safety locking device 120 is removed.

In addition, the plunger body 300 may be provided with stopper protrusions 320 to limit a range of movement to the second position. In response to the movement of the plunger body 300 to the second position, the stopper protrusions 320 can limit the movement of the plunger body 300 by engaging with a portion of the internal container 102. That is, the range of movement of the plunger body 300 is limited to the second position by the stopper protrusions 320. The plunger body 300 is not ejected from the main container 100 beyond this range of movement.

Here, as illustrated in FIG. 6, buffer members 1022 may be coupled to portions of the internal container 102, with which the stopper protrusions 320 of the plunger body 300 engage. The buffer members 1022 can absorb impacts occurring when the moving plunger body 300 engages with the internal container 102. The buffer members 1022 can minimize noise caused by the engagement of the moving plunger body 300 during the operation of the applicator and minimize reaction due to the collision of the plunger body 300. Accordingly, it is possible to accurately insert the sensor probe 521 into the body.

In addition, a sensor receptacle 301 is provided on one end portion of the plunger body 300. The sensor receptacle 301 accommodates the sensor module 20 inserted into the sensor receptacle 301. The sensor module 20 is inserted into and accommodated in the sensor receptacle 301, and moves linearly from the first position to the second position along with the plunger body 300. Due to the linear movement to the second position, the sensor probe 521 and the needle 550 of the sensor module 20 are inserted into the body.

Here, sensor fixing hooks 330 are mounted on peripheral portions of the sensor receptacle 301. The sensor fixing hooks 330 can engage with the sensor module 20, inserted into the sensor receptacle 301, to fix the sensor module 20. The sensor fixing hooks 330 are coupled to the sensor module 20 such that each of the fixing hooks 330 is rotatable about a rotary shaft 331. When the plunger body 300 is in the first position, the sensor fixing hooks 330 is pressed inwardly by the internal container 102 to engage with the sensor module 20. When the plunger body 300 is in the second position, the sensor fixing hooks 330 are released from the pressed state, thereby disengaging from the sensor module 20. In this regard, the internal container 102 is provided with a hook guide 140, which will be described in more detail later.

Figure 14:
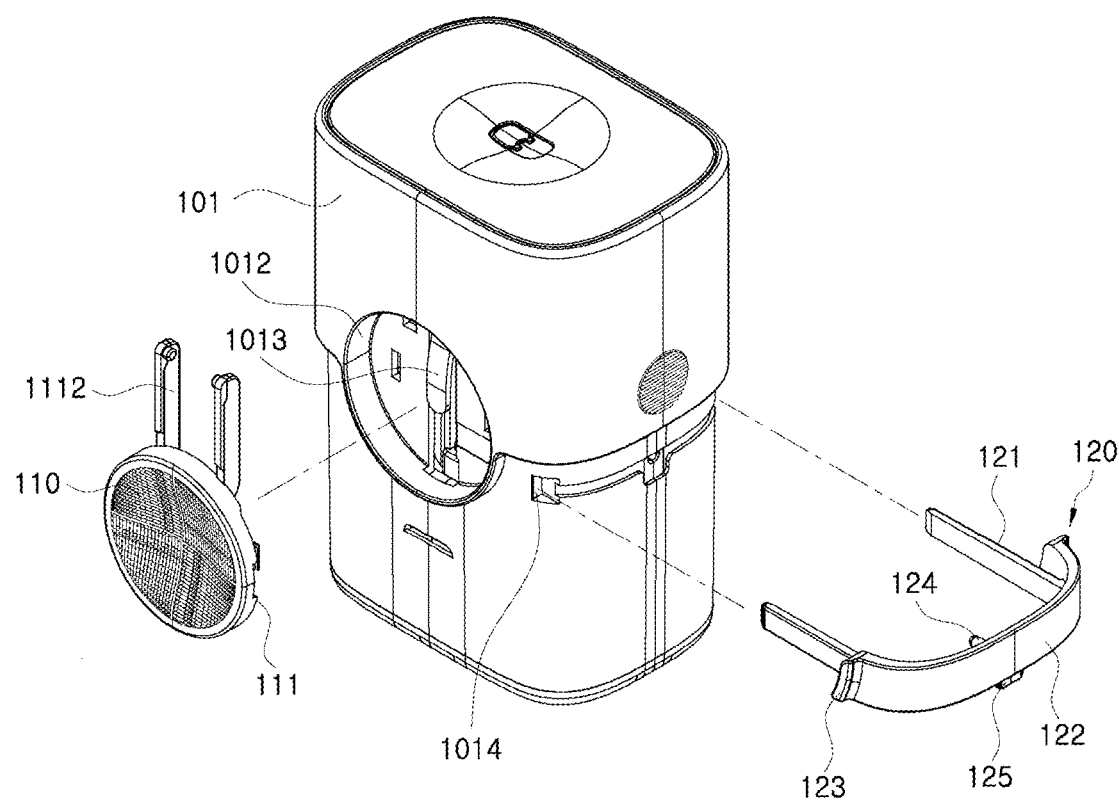
FIGS. 14 and 15 are perspective views schematically illustrating configurations of the press button and the safety locking device according to embodiments of the disclosure.

In addition, as illustrated in FIG. 14, the external container 101 is provided with a button guide opening 1012 into which the press button 110 is inserted. The button guide opening 1012 allows the inserted press button 110 to move when pressed. The pressing protrusions 111 are provided on the inner surface of the press button 110. In response to the pressed movement of the press button 110 in the button guide opening 1012 (or as the press button 110 in the button guide opening 1012 moves when pressed), the pressing protrusions 111 can press the elastic hooks 310 of the plunger body 300. The press button 110 is coupled to one end portion of the external container 101 via hinge rods 1112, such that press button 110 can pivot in a predetermined range. The press button 110 is configured to move by pivoting when pressed. A separate elastic member 1013 may be provided in the button guide opening 1012 to enable an elastic return function in response to the press button 110 being press-manipulated.

Figure 15:
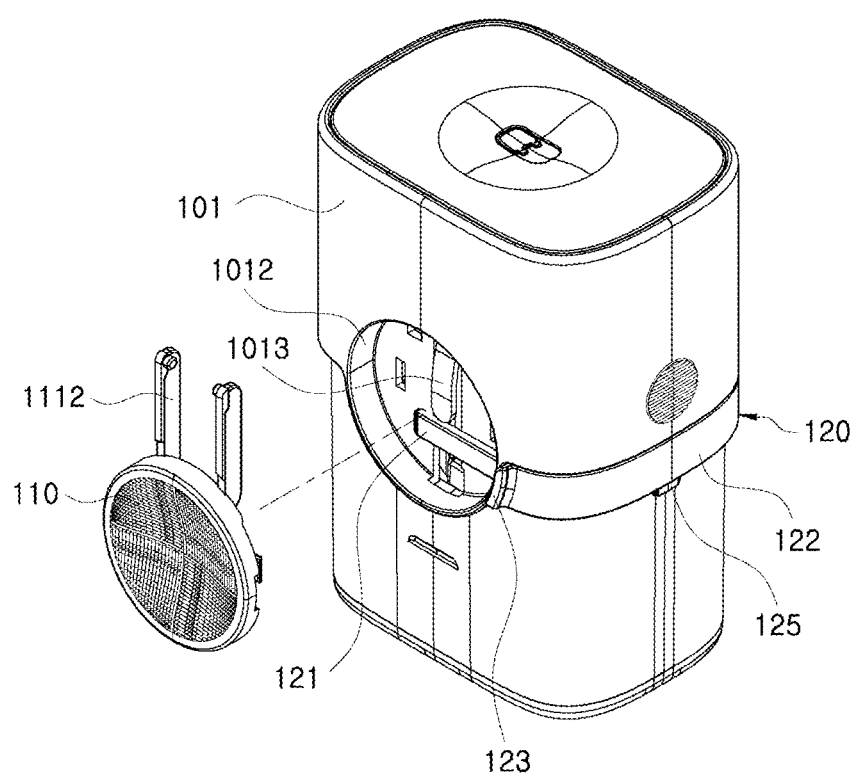

The safety locking device 120 able to prevent the press-manipulation performed to the press button 110 is coupled to the external container 101. As illustrated in FIGS. 14 and 15, the safety locking device 120 is slid into the button guide opening 1012 in a direction perpendicular to the depth direction of the button guide opening 1012 to prevent the pressed movement of the press button 110. Slide holes 1014 are provided in one portion of the external container 101, such that the safety locking device 120 is slid into the button guide opening 1012 through the slide holes 1014.

The safety locking device 120 includes anti-pressing rods 121 and an outer support 122. The anti-pressing rods 121 are configured to be inserted into and withdrawn from the button guide opening 1012 by sliding. The outer support 122 extends from one end of each of the anti-pressing rods 121, and is configured to surround an outer circumferential portion of the external container 101 in a state in which the anti-pressing rods 121 are inserted into the button guide opening 1012. When the anti-pressing rods 121 are inserted into the button guide opening 1012, the anti-pressing rods 121 are disposed to extend through the button guide opening 1012 in a direction perpendicular to the depth direction of the button guide opening 1012. Accordingly, the pressed movement of the press button 110 in the depth direction of the button guide opening 1012 is restrained.

Gripping protrusions 123 may protrude outward from the outer support 122 of the safety locking device 120, such that the user can hold the gripping protrusions 123 with a hand when the user intends to slide and withdraw the safety locking device 120. A guide protrusion 124 may protrude from a side surface portion of the outer support 122. During sliding insertion, the guide protrusion 124 may be fitted into, while extending through, the external container 101 to accurately guide the safety locking device 120 to the insertion position.

In addition, the safety locking device 120 may be configured so as not to be decoupled from the main container 100 unless the protective cap 200 is decoupled from the main container 100. This is because, if the safety locking device 120 is decoupled and the press button 110 is pressed in a state in which the protective cap 200 is not detached, the sensor probe 521 may be damaged through collision with the protective cap 200.

Accordingly, an engagement extension 125 may be provided on the outer support 122 of the safety locking device 120 to extend perpendicularly to the direction in which the anti-pressing rods 121 are slid. Accordingly, as the protective cap 200 is coupled to the external container 101 in a state in which the outer support 122 is coupled to the external container 101 while surrounding an outer surface portion of the external container 101, the engagement extension 125 may engage with the protective cap 200.

Figure 16A:
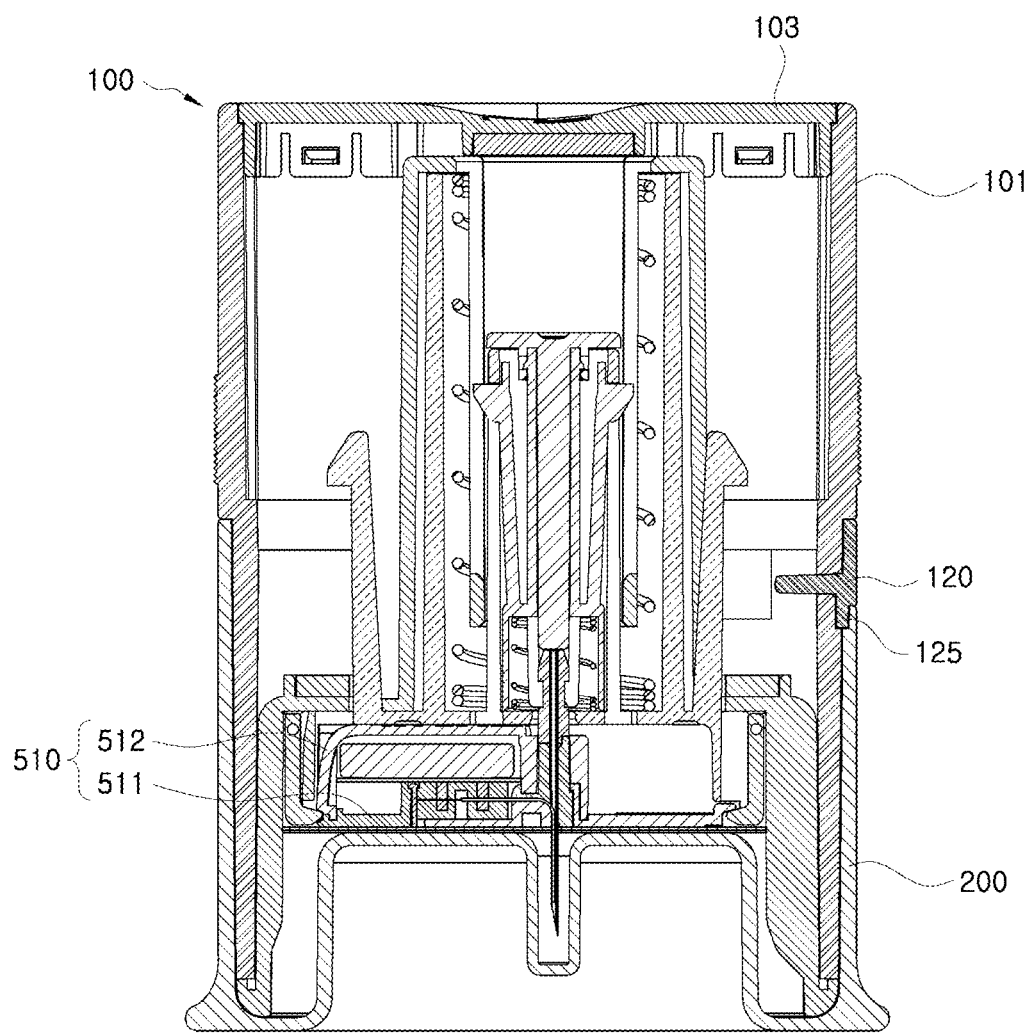
FIGS. 16A and 16B are views illustrating a coupling structure of the safety locking device and the protective cap according to embodiments of the disclosure.
Figure 16B:
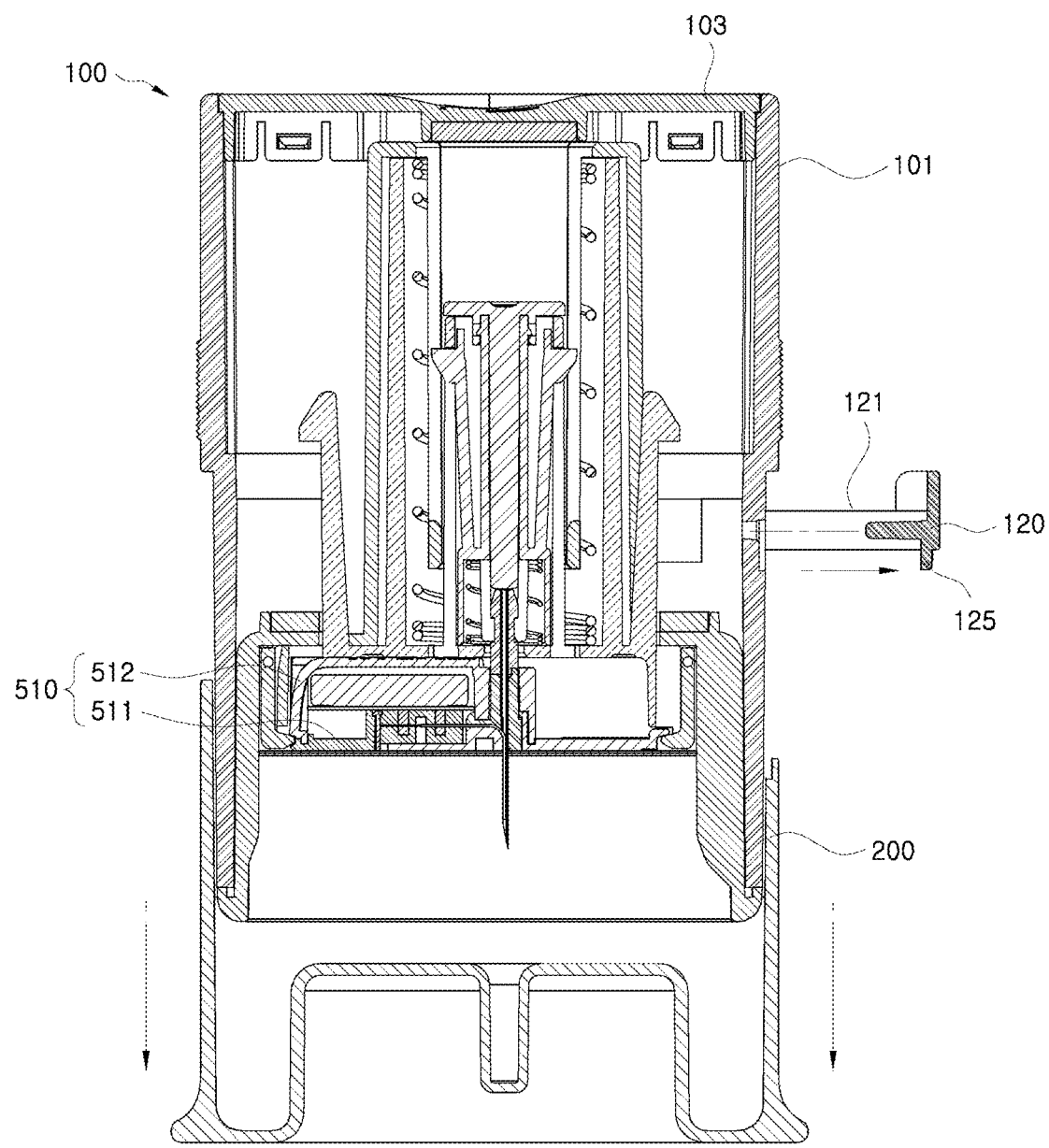

According to this structure, as illustrated in FIG. 16a, in a state in which the safety locking device 120 is slid into the external container 101, if the protective cap 200 is not detached and removed, the engagement extension 125 of the safety locking device 120 cannot remain engaged with the top end portion of the protective cap 200, so that the safety locking device 120 cannot be removed from the external container 101. As illustrated in FIG. 16b, if the protective cap 200 is detached and removed, the engagement extension 125 of the safety locking device 120 is disengaged. Accordingly, it is possible to slide and withdraw the safety locking device 120 from the external container 101, so that the safety locking device 120 is removed.

In addition, the applicator 10 is configured such that, in the first position in which the sensor module 20 is preinstalled therein, the sensor module 20 remains fixedly coupled to the sensor module 20, and in the second position in which the sensor module 20 is ejected, the sensor module 20 is decoupled from the sensor module 20.

Figure 17:
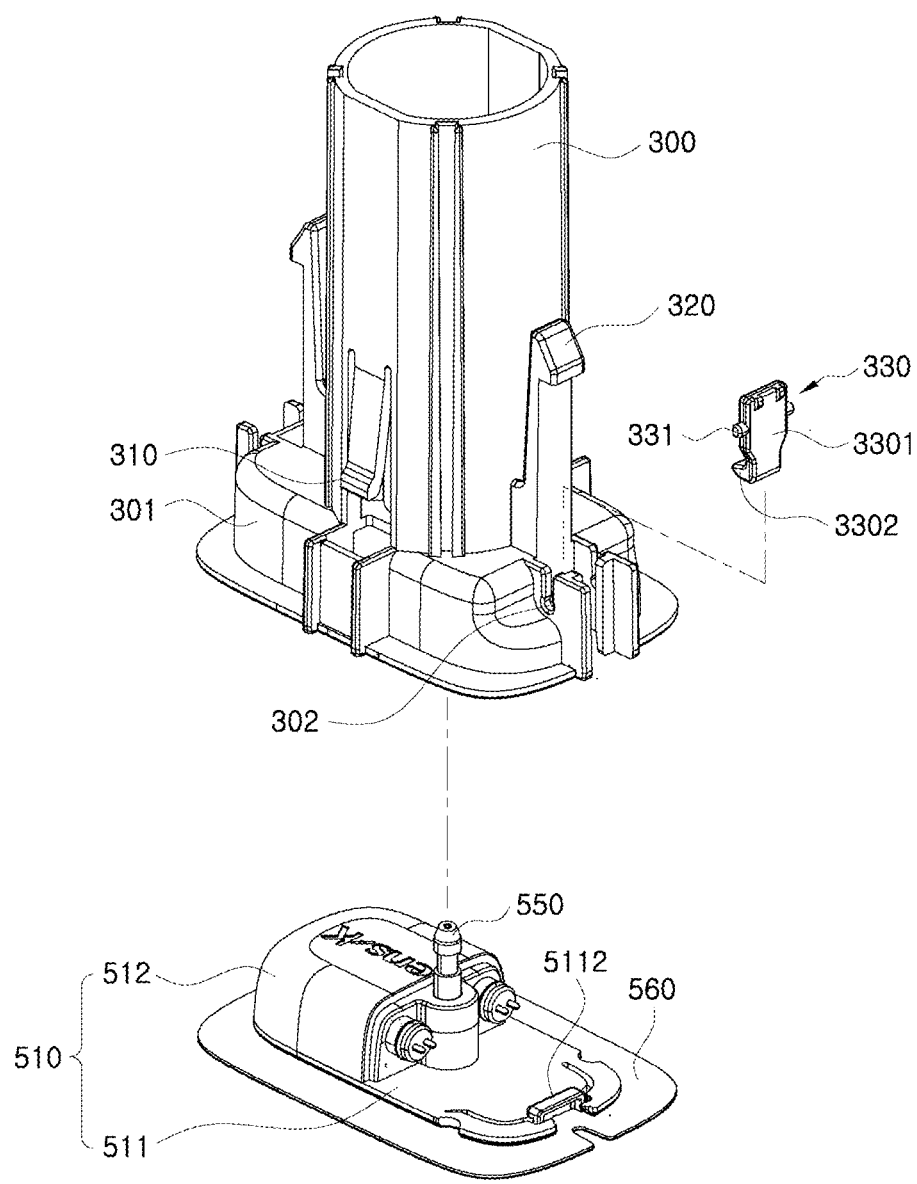
FIG. 17 is a view illustrating a configuration of the sensor fixing hooks of the plunger body according to embodiments of the disclosure.

As described above, the sensor fixing hooks 330 are mounted on the circumferential portions of the sensor receptacle 301 of the plunger body 300, as illustrated in FIG. 17. The sensor fixing hooks 330 can engage with the sensor module 20, inserted into the sensor receptacle 301, to be fixedly coupled to the sensor module 20. Each of the coupled sensor fixing hooks 330 is rotatable about the rotary shaft 331. When the plunger body 300 is in the first position, the sensor fixing hooks 330 are pressed inwardly by the internal container 102 to be engaged with the sensor module 20. When the plunger body 300 is in the second position, the sensor fixing hooks 330 are released from the pressed state, thereby being disengaged from the sensor module 20. In this regard, the hook guide 140 is provided on the internal container 102.

As illustrated in FIG. 17, each of the sensor fixing hooks 330 may include a pivot body 3301 on which the rotary shaft 331 is provided and a hook protrusion 3302 protruding from the bottom end portion of the pivot body 3301 to engage with the sensor module 20. The plunger body 300 has rotary shaft coupling recesses 302 to which the rotary shafts 331 of the sensor fixing hooks 330 are coupled. In addition, engagement recesses 5112 conforming to the sensor fixing hooks 330 are formed in both end portions of the pod base 511 of the sensor module 20 to engage with the hook protrusions 3302 of the sensor fixing hooks 330 in a state in which sensor module 20 is inserted into the sensor receptacle 301.

The hook guide 140 protrudes inward from the inner surface of the internal container 102 in the top-bottom direction. The inner surface of the hook guide 140 is comprised of a protruding surface 141 and a concave surface 142. The protruding surface 141 presses the sensor fixing hooks 330, while the concave surface 142 releases the sensor fixing hooks 330 from the pressed state. The concave surface 142 is configured to release the sensor fixing hooks 330 from the pressed state when the sensor fixing hooks 330 have moved to the second position together with the plunger body 300. That is, the protruding surface 141 protrudes relatively inward to press the sensor fixing hooks 330 during the movement along a path between the first position and directly before the second position. Since the concave surface 142 is relatively concave, the concave surface 142 releases the sensor fixing hooks 330 from the pressed state when the plunger body 300 is in the second position.

Figure 18A:
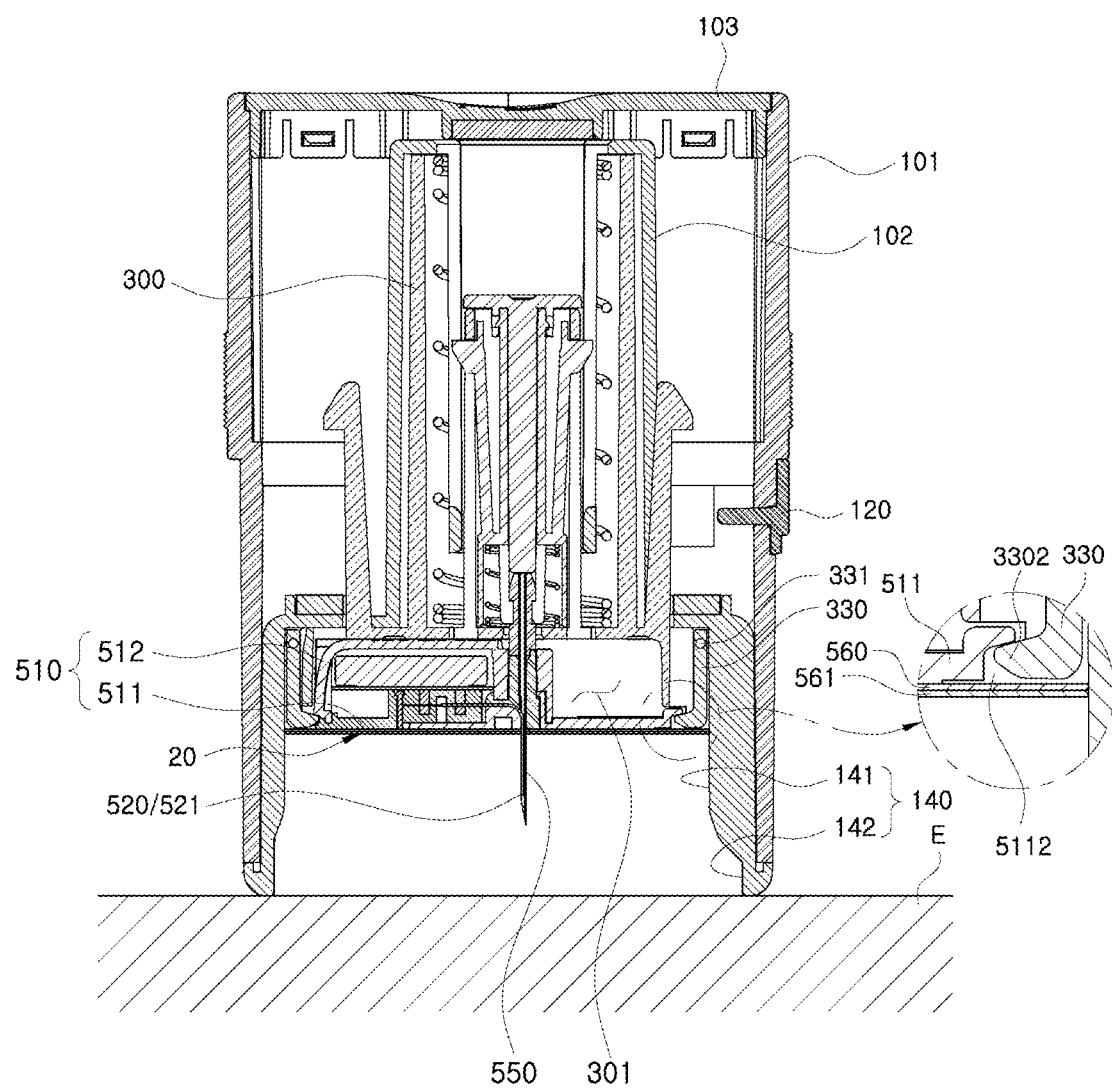
FIGS. 18A and 18B are views illustrating a separation structure of the applicator and the sensor module according to embodiments of the disclosure.
Figure 18B:
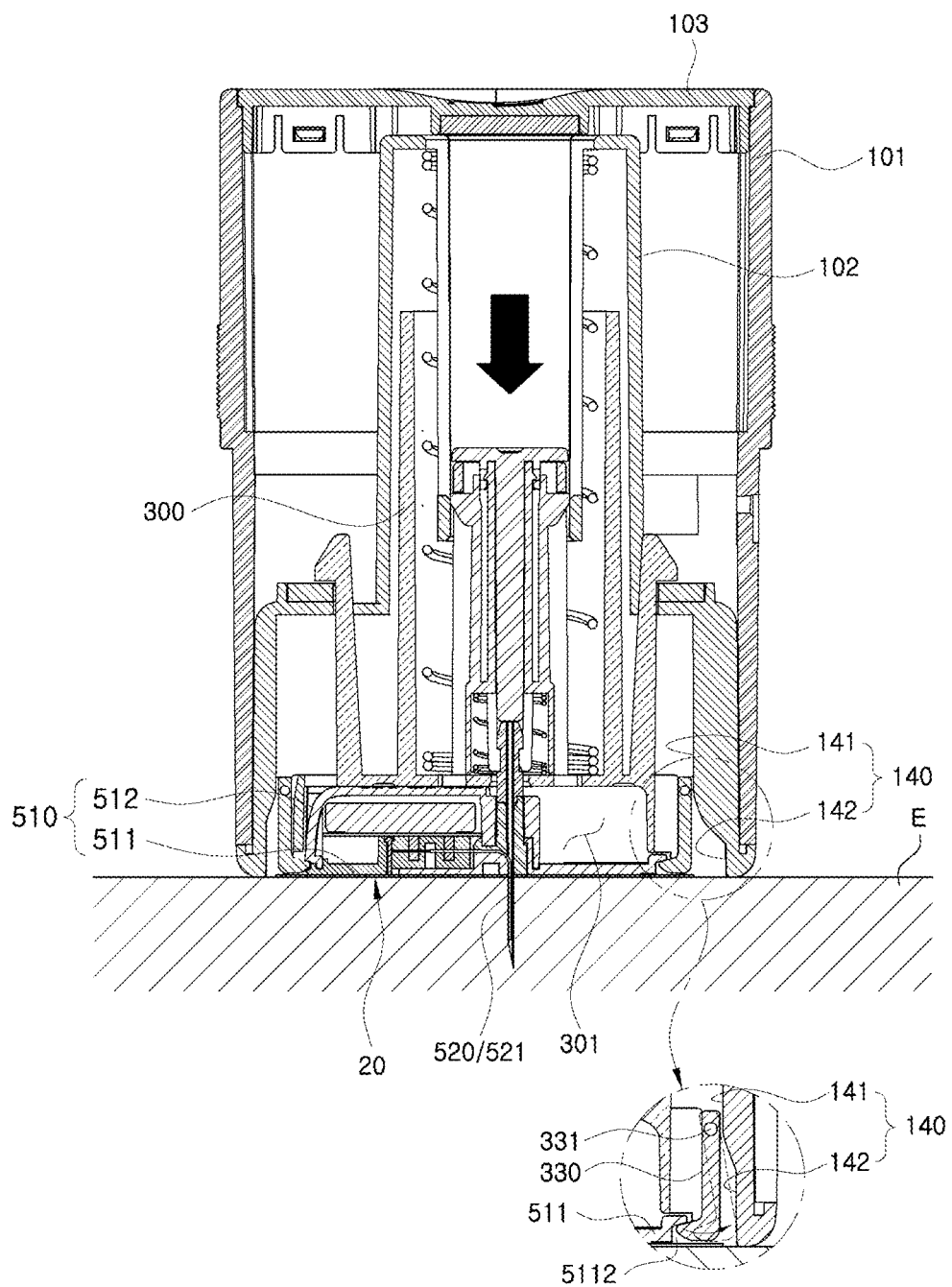

Accordingly, as illustrated in FIG. 18a, when the plunger body 300 is in the first position, the sensor fixing hooks 330 are pressed inwardly by the protruding surface 141 of the hook guide 140 to engage with the sensor module 20 accommodated in the sensor receptacle 301. As illustrated in FIG. 18b, when the plunger body 300 is moved linearly to the second position, the concave surface 142 of the hook guide 140 releases the sensor fixing hooks 330 from the pressed state, so that the sensor fixing hooks 330 can pivot about the rotary shaft 331 to disengage from the sensor module 20. In this situation, i.e. in a situation in which the plunger body 300 has moved to the second position together with the sensor module 20, the sensor module 20 is attached to the skin by the adhesive tape 560. In this state, when the applicator 10 is detached away from the human body, the sensor fixing hooks 330 are disengaged from the sensor module 20, so that the applicator 10 is detached from the human body, and the sensor module 20 remains attached to the human body.

In addition, according to the disclosure, the applicator 10 and the sensor module 20 are fabricated, with the sensor module 20 being preinstalled in the applicator 10. Accordingly, as described above, reuse, i.e. inserting another sensor module 20 into the applicator 10, is prevented.

In this regard, an anti-return means for preventing the plunger body 300 from returning to the first position after having moved to the second position is provided in the main container 100.

Figure 19A:
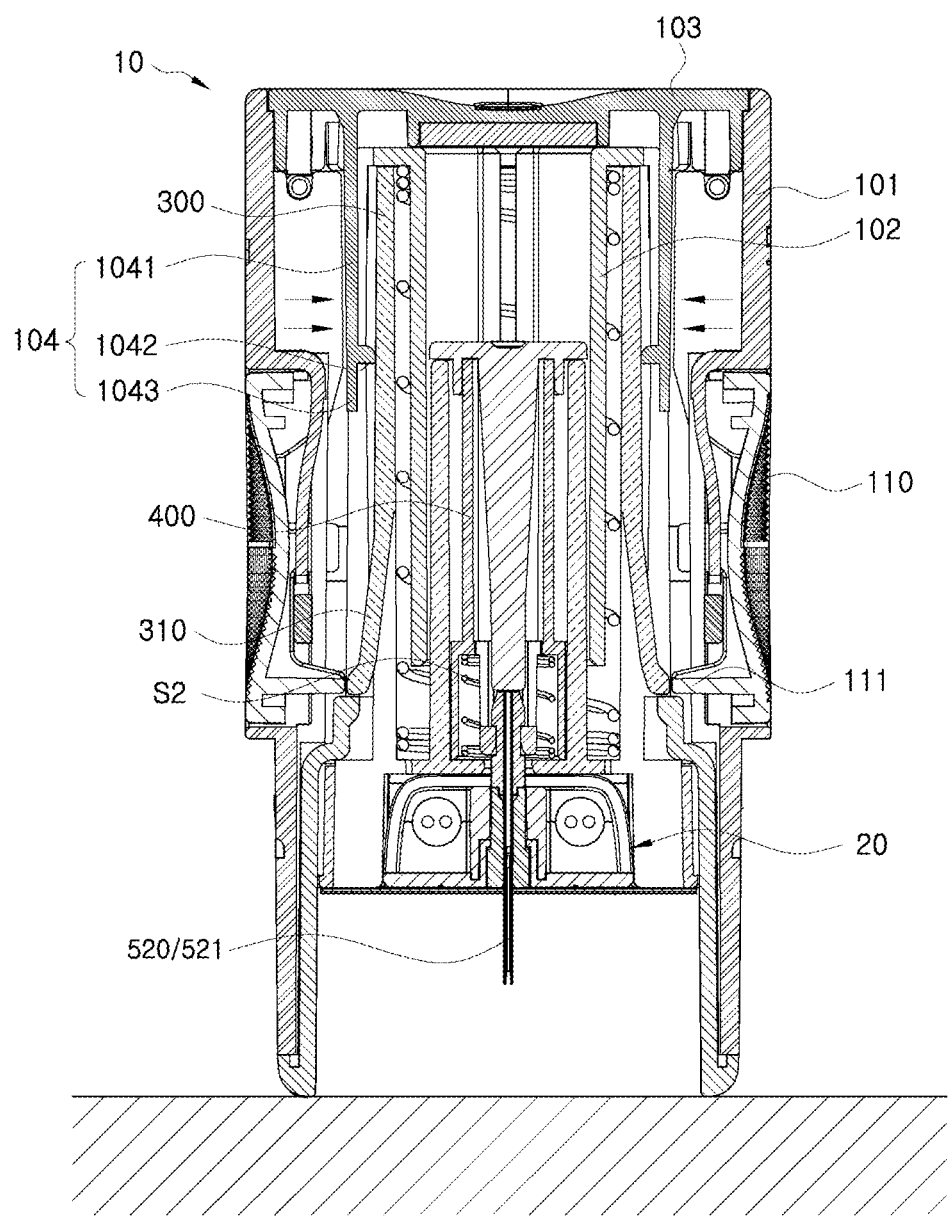
FIGS. 19A and 19B are views illustrating a reuse prevention structure of the applicator according to embodiments of the disclosure.
Figure 19B:
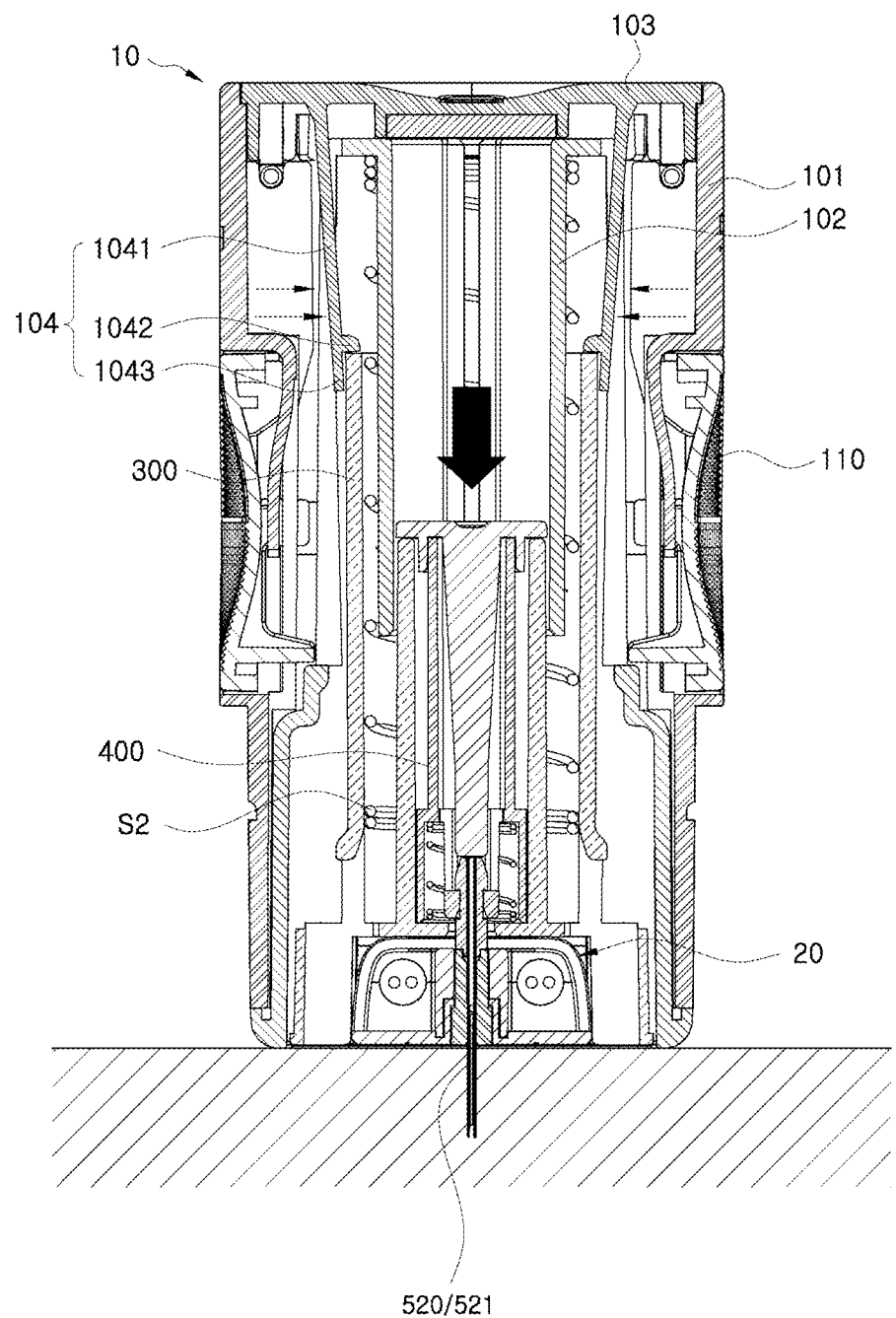

The anti-return means may include the anti-return hooks 104 elastically supported in a direction, in which the outer surface of the plunger body 300 is pressed, to engage with the top end portion of the plunger body 300 when the downward movement of the plunger body 300 from the first position to the second position is completed, as illustrated in FIGS. 19a and 19b.

Figure 20:
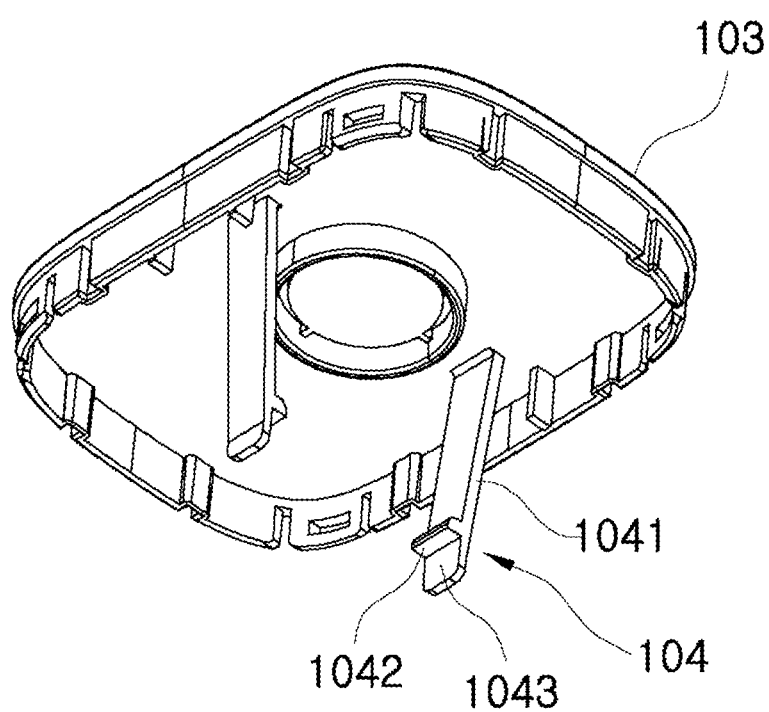
FIG. 20 is a perspective view schematically illustrating a configuration of the anti-return hooks of the applicator according to embodiments of the disclosure.

As illustrated in FIG. 20, each of the anti-return hooks 104 may include an elastic body 1041 formed of an elastic material and a hook portion 1042. The elastic body 1041 extends downward from the inner top portion of the main container 100. The hook portion 1042 protrudes from the bottom end portion of the elastic body 1041. The elastic body 1041 may be formed integrally with the bottom surface of the container cover 103 coupled to the top end portion of the external container 101 of the main container 100. In addition, the elastic body 1041 may have an elastically offset structure, i.e. the elastic body 1041 may be inclined toward the center axis in the direction of the bottom end, such that the hook portion 1042 can elastically press an outer surface portion of the plunger body 300.

When the plunger body 300 is in the first position, the hook portions 1042 elastically press outer surface portions of the plunger body 300 due to the elastic force of the elastic bodies 1041. When the plunger body 300 is in the second position, the hook portions 1042 are elastically moved toward the center axis by the elastic force of the elastic body 1041 to engage with the top end portion of the plunger body 300.

Here, a stopper 1043 is provided on the bottom end portion of each of the elastic bodies 1041. When the plunger body 300 is in the second position, the stoppers 1043 may be elastically moved by the elastic force of the elastic bodies 1041 to come into contact with outer surface portions of the plunger body 300, thereby limiting the distance of the elastic movement of the elastic bodies 1041.

According to the stoppers 1043 configured as above, in the process in which the elastic bodies 1041 elastically move toward the center in the second position of the plunger body 300, the movement of the stoppers 1043 is restrained through contact with the outer surface portions of the plunger body 300. In this position, the hook portions 1042 engage with the top end portion of the plunger body 300. That is, the stoppers 1043 can limit excessive elastic movement of the elastic bodies 1041, thereby guide accurate engagement between the hook portions 1042 and the plunger body 300. In addition, even in the case in which the elastic kinetic force of the elastic bodies 1041 is significantly increased, the movement of the elastic bodies 1041 is restrained in a proper position. Accordingly, the elastic bodies 1041 can move more rapidly due to the increased elastic movement speed thereof, and thus, the anti-return operation can be performed reliably.

In addition, the applicator 10 is configured to withdraw and remove the needle 550 of the sensor module 20 from the body at the moment that the ejection movement of the sensor module 20 from the first position to the second position is completed. In this regard, the applicator 10 may include a needle withdrawing means N for withdrawing and removing the needle 550 from the body by moving the needle 550 upwardly at the moment that the movement of the plunger body 300 from the first position to the second position is completed.

The needle withdrawing means N may further include a needle withdrawing body 400 and a needle withdrawing elastic spring S2. The needle withdrawing body 400 is coupled to the needle head 551 of the needle 550 and engaged with the plunger body 300 to move linearly from the first position to the second position along with the plunger body 300 within the internal container 102. The needle withdrawing elastic spring S2 applies elastic force to the needle withdrawing body 400 in a direction in which the needle withdrawing body 400 moves upwardly toward the first position.

The needle withdrawing body 400 is engaged with the plunger body 300. In this regard, the needle withdrawing body 400 has separate elastic hooks 410 that are elastically deformable. The elastic hooks 410 are elastically offset in a direction of engagement with a hook engaging portion 340 of the plunger body 300. Accordingly, when the plunger body 300 moves linearly from the first position to the second position in response to the press button 110 being manipulated, the needle withdrawing body 400 also moves linearly to the second position together with the plunger body 300.

Here, the internal container 102 is provided with a needle withdrawing pressing portion 130. In response to the movement of the needle withdrawing body 400 to the second position, the needle withdrawing pressing portion 130 presses the elastic hooks 410 inwardly so that the elastic hooks 410 are disengaged from the hook engaging portion 340 of the plunger body 300.

According to this structure, when the press button 110 is press-manipulated, the needle withdrawing body 400 moves from the first position to the second position together with the plunger body 300. At the same time, the elastic hooks 410 of the needle withdrawing body 400 is pressed by the needle withdrawing pressing portion 130 of the internal container 102 to be disengaged from the hook engaging portion 340. Then, due to the elastic force of the withdrawing elastic spring S2, the needle withdrawing body 400 returns upwardly to the first position.

Here, the needle withdrawing body 400 is coupled to the needle head 551 of the needle 550 via a needle head coupling portion 420 provided on one end portion thereof. During the upward return movement of the needle withdrawing body 400, the needle 550 moves along with the needle withdrawing body 400 to be withdrawn and removed from the body. The needle head coupling portion 420 is provided on the bottom end portion of the needle withdrawing body 400 to engage with the coupling recess 552 of the needle head 551.

The needle withdrawing body 400 can be moved upwardly to the top end portion of the inner surface of the main container 100 by the elastic force of the withdrawing elastic spring S2, instead of being moved upwardly to the first position. In this case, the needle withdrawing body 400, driven by the elastic force, may create impacts while colliding with the top end portion of the inner surface of the main container 100. To reduce such impacts, a buffer member 1031 may be provided on the top end portion of the inner surface of the main container 100. Since the buffer member 1031 can minimize noise, users' worries about the operation of the device may be eliminated. The buffer member 1031 may be coupled to the container cover 103 provided in the top end portion of the main container 100.

In addition, in response to the movement of the plunger body 300 to the second position by the elastic force of the elastic plunger spring S1, the sensor probe 521 and the needle 550 of the sensor module 20 are inserted into the human body. During the insertion of the needle 550 into the human body, resistance to the insertion may generate reaction force, by which the needle 550 may be moved backwardly in the direction opposite to the direction in which the needle 550 is inserted into the human body. In this case, since the sensor probe 521 may not be inserted into the body to a proper depth, it may be preferred that the backward movement of the needle 550 is prevented. In this regard, a needle support block 430 may be coupled to the needle withdrawing body 400. The needle support block 430 may support the top end portion of the needle 550 so that the needle 550 does not move upwardly with respect to the needle withdrawing body 400.

Next, the use of the above-described sensor applicator assembly will be described with reference to FIGS. 21 to 24.

FIGS. 21 to 24 are views sequentially illustrating the use of the sensor applicator assembly for a continuous glucose monitoring system according to embodiments of the disclosure, in a stepwise manner.

Figure 21:
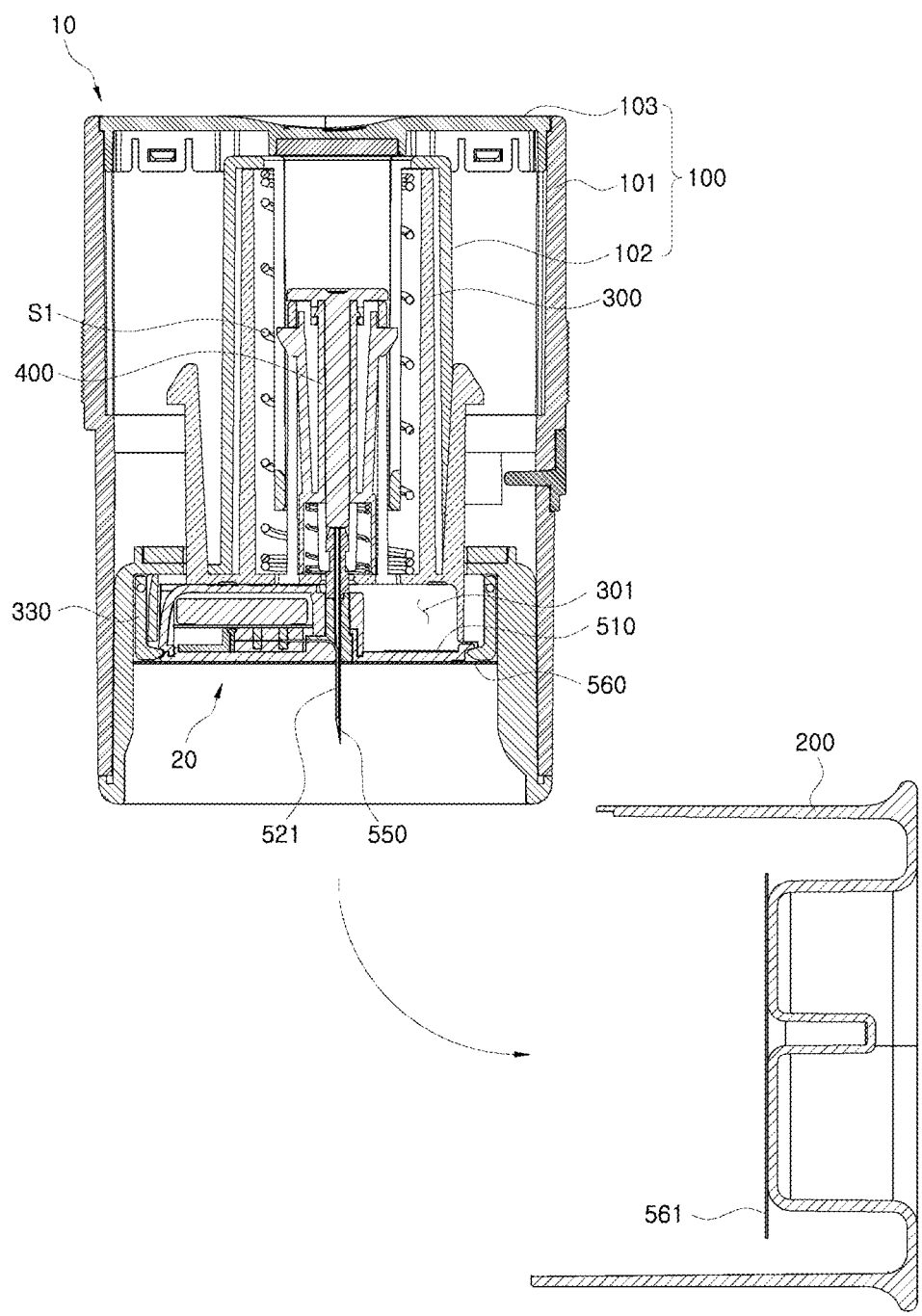
FIGS. 21 to 24 are views sequentially illustrating the use of the sensor applicator assembly for a continuous glucose monitoring system according to embodiments of the disclosure, in a stepwise manner.

First, as illustrated in FIG. 21, the protective cap 200 of the applicator 10 is detached. In the process in which the protective cap 200 is detached, the release paper 561 of the adhesive tape 560 of the sensor module 20 is detached together with the protective cap 200, thereby being removed from the adhesive tape 560. Afterwards, the sensor applicator assembly is located on a portion of the body, to which the sensor module 20 is to be attached. In this state, the safety locking device 120 is removed from the sensor applicator assembly.

Figure 22A:
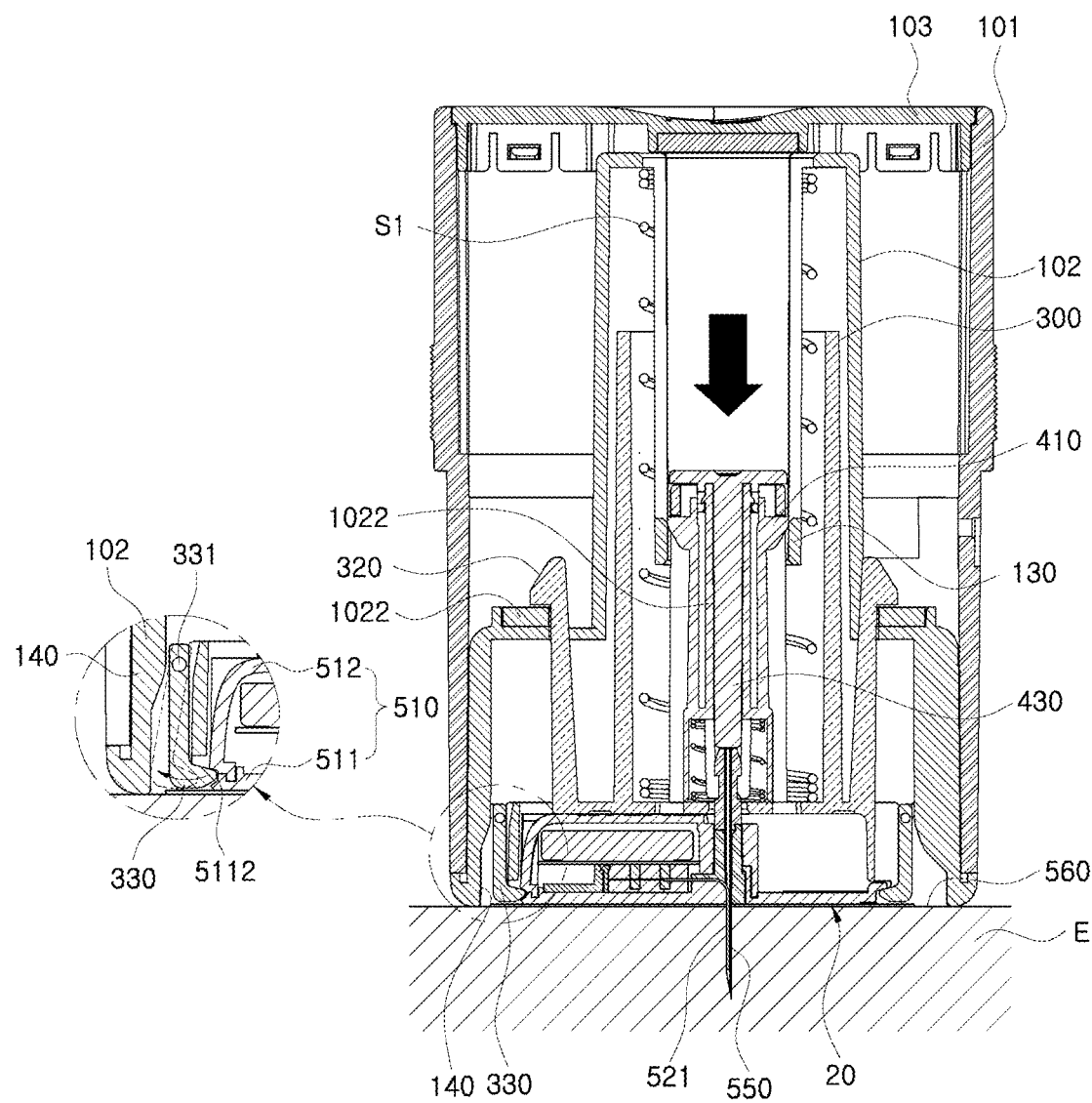
Figure 22B:
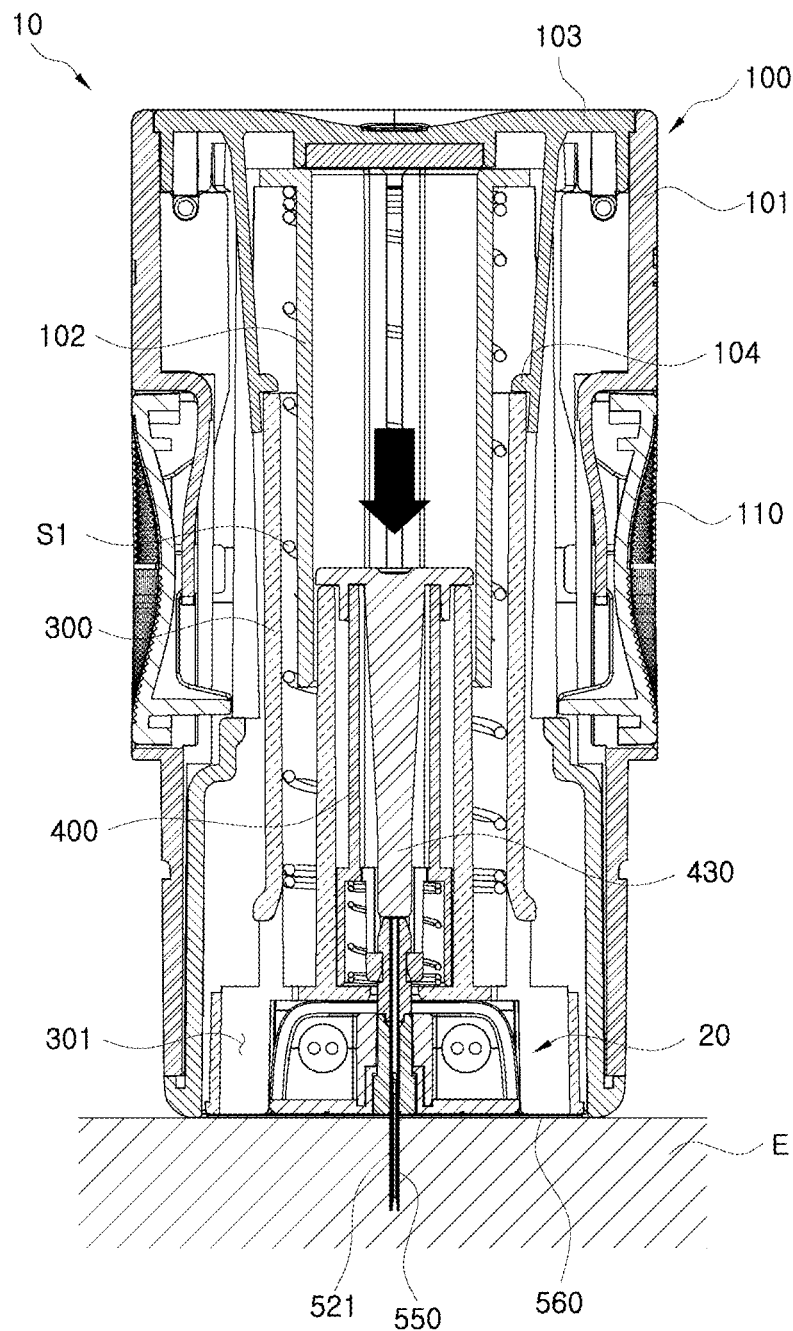

When the press button 110 is press-manipulated in a state in which the safety locking device 120 is removed, the plunger body 300 is moved downwardly in an ejecting direction by the elastic plunger spring S1, as illustrated in FIGS. 22a and 22b. In this process, the needle 550 and the sensor probe 521 of the sensor module 20 are inserted into the body E. Here, the sensor module 20 is bonded to the surface of the body E via the adhesive tape 560. When the plunger body 300 is moved in the ejecting direction, the plunger body 300 cannot move upwardly again, engaged by the anti-return hooks 104 of the external container 101. Accordingly, after the applicator 10 is used once, the applicator 10 cannot be reused.

When the plunger body 300 is moved downwardly, as illustrated in FIG. 22a, the sensor fixing hooks 330 of the sensor receptacle 301 are released from the pressed state by the concave surface 142 of the hook guide 140, thereby being disengaged from the sensor module 20. In addition, the elastic hooks 410 of the needle withdrawing body 400 are pressed inwardly by the needle withdrawing pressing portion 130 of the internal container 102, thereby being disengaged from the plunger body 300.

Figure 23:
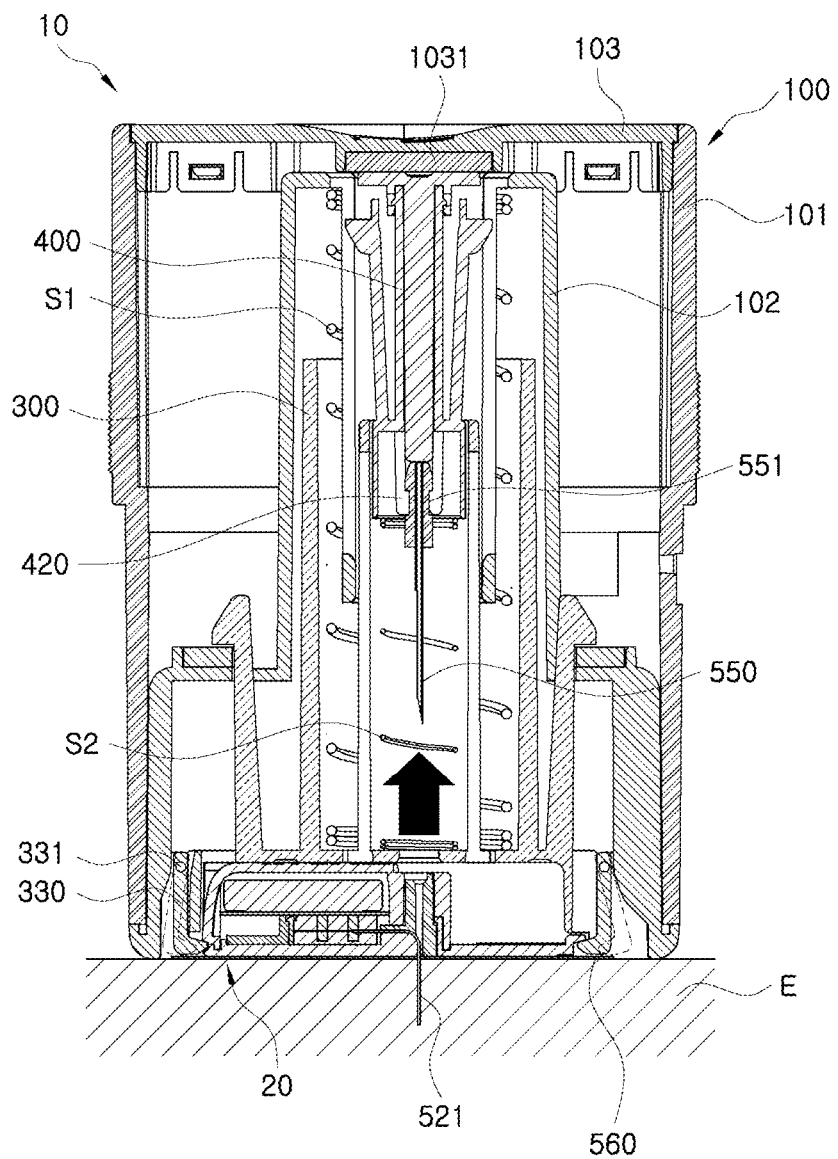

Accordingly, when the plunger body 300 is moved downwardly, the needle withdrawing body 400 is simultaneously returned upwardly by the withdrawing elastic spring S2, as illustrated in FIG. 23. Here, the needle 550 is moved upwardly along with the needle withdrawing body 400, so that the needle 550 is withdrawn and removed from the body E.

Figure 24:
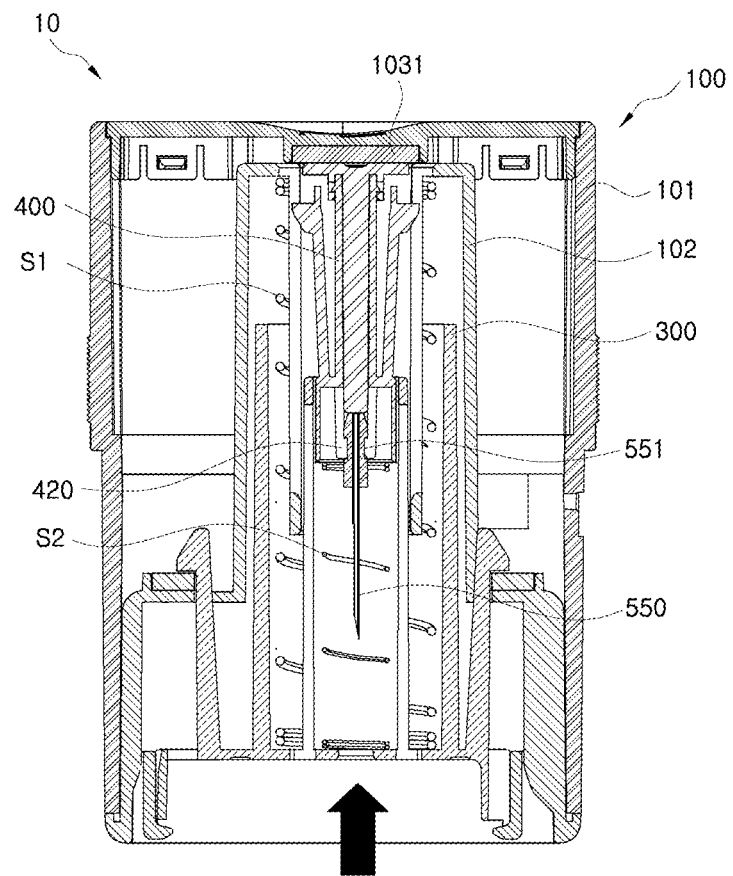
Figure 24:
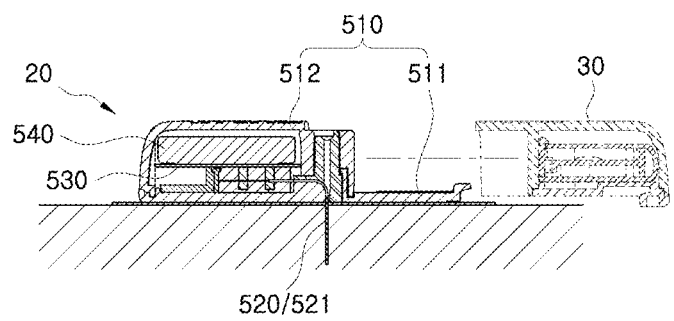

In this state, the sensor fixing hooks 330 is disengaged from the sensor module 20 as described above. As illustrated in FIG. 24, the applicator 10 can be detached and removed upwardly. When the applicator 10 is detached and removed in this manner, only the sensor module 20 remains attached to the body E. Afterwards, the transmitter 30 is coupled to the sensor module 20 so as to be connected to the connector terminal 513, and the transmitter 30 transmits a glucose measurement result, obtained by the sensor module 20, to the user terminal.

The foregoing descriptions have been presented in order to explain certain principles of the present disclosure by way of example. A person skilled in the art to which the present disclosure relates could make various modifications and variations without departing from the essential features of the present disclosure. The foregoing embodiments disclosed herein shall be interpreted as being illustrative, while not being limitative, of the principle and scope of the present disclosure. It should be understood that the scope of the present disclosure shall be defined by the appended Claims and all of their equivalents fall within the scope of the present disclosure.

The invention claimed is:

1. A sensor applicator assembly for a glucose monitoring system, the sensor applicator assembly being assembled as a single unitary product in which a sensor module for measuring a blood glucose level is preinstalled in an applicator, such that the sensor module is ejected by an operation of the applicator to be attached to a human body,
wherein the applicator has a press button mounted thereon to be press-manipulated by a user, and a separate safety locking device is coupled to prevent the press button from being press-manipulated, wherein the press button is allowed to be press-manipulated after the safety locking device is removed,
a button guide opening, into which the press button is inserted, is provided at an outer circumferential surface of the applicator, the button guide opening allowing the inserted press button to move in a direction perpendicular to an ejection direction of the sensor module when the inserted press button is press-manipulated in a state that the safety locking device is removed from the button guide opening, and
the safety locking device is configured to be slidably inserted into the button guide opening in a direction perpendicular to a moving direction of the press button and be interlocked with the press button to prevent the press button from moving when the press button is press-manipulated in a state that the safety locking device is inserted to the button guide opening, and slide holes, through which the safety locking device is slid into the button guide opening, are provided at the outer circumferential surface of the applicator, and the press button is configured to be allowed to be press-manipulated only when the safety locking device is removed from the button guide opening.

2. The sensor applicator assembly according to claim 1, wherein the applicator includes:
a main container having an accommodation space therein and an open side, with the press button being mounted on the main container to be press-manipulated by a user;
a plunger body disposed in a first position within the main container to move linearly from the first position to a second position in an ejecting direction in response to the press button being manipulated; and
an elastic plunger spring applying elastic force to the plunger body so that the plunger body moves linearly from the first position to the second position,
wherein the sensor module is coupled to the plunger body to move from the first position to the second position, integrally with the plunger body, and
the safety locking device is coupled to the main container.

3. The sensor applicator assembly according to claim 1, wherein the safety locking device includes:
anti-pressing rods configured to be inserted into and withdrawn from the button guide opening by sliding; and
an outer support extending from one end of each of the anti-pressing rods and surrounds an outer circumferential surface of an external container, with the anti-pressing rods being inserted into the button guide opening,
wherein, as the anti-pressing rods are inserted into the button guide opening, the press button is prevented from moving when pressed.

4. The sensor applicator assembly according to claim 3, wherein the outer support has a gripping protrusion protruding outward.

5. The sensor applicator assembly according to claim 3, wherein a separate protective cap is detachably coupled to a main container to block the sensor module, inserted into the main container, from being exposed externally, and
when the protective cap is coupled to the main container, the safety locking device is prevented from being decoupled from the main container.

6. The sensor applicator assembly according to claim 5, wherein an engagement extension is provided on the outer support to extend perpendicularly to a sliding direction of the anti-pressing rods, such that, as the protective cap is coupled to the external container in a state in which the outer support is coupled to the external container while surrounding an outer surface of the external container, the engagement extension engages with the protective cap.

7. The sensor applicator assembly according to claim 1, wherein the safety locking device has a separate structure from the applicator, and the safety locking device is configured to be detachably coupled to the applicator.

* * * * *